United States Patent
Androsch et al.

(10) Patent No.: US 12,364,405 B1
(45) Date of Patent: Jul. 22, 2025

(54) HEMODYNAMIC DETERMINATION OF ARTERIAL STIFFNESS, ARTERIAL AGE, ARTERIAL DEPOSITS AND HBA1C

(71) Applicant: Quantum BioTek Inc., Atlanta, GA (US)

(72) Inventors: Astrid Androsch, Atlanta, GA (US); David Yuan, Atlanta, GA (US); Vladimir Fridman, Atlanta, GA (US); Jacob Androsch, Atlanta, GA (US); Frederick Nii Ofei Bruce, Atlanta, GA (US); Simon Androsch, Atlanta, GA (US)

(*) Notice: Subject to any disclaimer, the term of this patent is extended or adjusted under 35 U.S.C. 154(b) by 0 days.

(21) Appl. No.: 18/233,972

(22) Filed: Aug. 15, 2023

Related U.S. Application Data

(63) Continuation-in-part of application No. 29/884,194, filed on Feb. 8, 2023, and a continuation-in-part of
(Continued)

(51) Int. Cl.
*A61B 5/1455* (2006.01)
*A61B 5/00* (2006.01)
(Continued)

(52) U.S. Cl.
CPC ........ *A61B 5/02125* (2013.01); *A61B 5/0062* (2013.01); *A61B 5/0082* (2013.01);
(Continued)

(58) Field of Classification Search
CPC . A61B 5/02125; A61B 5/0062; A61B 5/0082; A61B 5/02007; A61B 5/02028;
(Continued)

(56) References Cited

U.S. PATENT DOCUMENTS 9,775,528 B2   10/2017   Vermeulen et al.
9,814,397 B2   11/2017   Inan et al.
(Continued)

FOREIGN PATENT DOCUMENTS

EP   3841966   6/2021
WO   WO2012/037679   3/2012
(Continued)

OTHER PUBLICATIONS

Meridian Ditigal Pulse Analyzer webpage https://digitalpulseanalyzer.com/ retrieved Feb. 15, 2024.
(Continued)

*Primary Examiner* — Chu Chuan Liu
(74) *Attorney, Agent, or Firm* — Gugliotta & Gugliotta LPA

(57) ABSTRACT

An advanced cardiovascular health monitoring system utilizes an optical pulse wave velocity detection device in combination with a system for analyzing data waveforms structures in combination with personalized patient data integration to determine specific physiological parameters for monitoring and assessing specific health conditions. Using acceleration pulse waves, vascular health is calculated by the ratio of peak to the second derivative of blood volume pulse wave, which can detect various health indices such as vascular age, vascular health index, and arteriosclerosis. The device collects separate pulse points within a time interval. It connects them into a line to form the PPG Image, which is then analyzed through data filtering and fitting methods. The periodic cycle acquisition method excludes abnormal cycle data and ensures correct data acquisition. Artificial Intelligence and data analytics are aiding the software to improve and optimize underlying data ranges continuously; the algorithms are summarized in figures. The invention may be used as part of non-invasive screening testing.

8 Claims, 21 Drawing Sheets

Related U.S. Application Data application No. PCT/US2023/010739, filed on Jan. 13, 2023, and a continuation-in-part of application No. 17/523,754, filed on Dec. 22, 2021, now abandoned, and a continuation-in-part of application No. 17/543,702, filed on Dec. 6, 2021, now abandoned.

(51) Int. Cl.
| | |
|---|---|
| *A61B 5/02* | (2006.01) |
| *A61B 5/0205* | (2006.01) |
| *A61B 5/021* | (2006.01) |
| *G06F 18/231* | (2023.01) |
| *G16H 50/20* | (2018.01) |
| *G16H 50/50* | (2018.01) |
| *A61B 5/024* | (2006.01) |

(52) U.S. Cl.
CPC ...... *A61B 5/02007* (2013.01); *A61B 5/02028* (2013.01); *A61B 5/0205* (2013.01); *A61B 5/02116* (2013.01); *A61B 5/6826* (2013.01); *A61B 5/7207* (2013.01); *A61B 5/7239* (2013.01); *A61B 5/7246* (2013.01); *A61B 5/7275* (2013.01); *A61B 5/7278* (2013.01); *G06F 18/231* (2023.01); *G16H 50/20* (2018.01); *G16H 50/50* (2018.01); *A61B 5/0022* (2013.01); *A61B 5/02433* (2013.01); *A61B 5/14552* (2013.01); *A61B 2560/02* (2013.01); *A61B 2560/0406* (2013.01); *A61B 2560/0462* (2013.01); *A61B 2562/0238* (2013.01); *A61B 2562/146* (2013.01); *A61B 2562/227* (2013.01)

(58) Field of Classification Search
CPC ............ A61B 5/0205; A61B 5/021116; A61B 5/6826; A61B 5/7207; A61B 5/7239; A61B 5/7246; A61B 5/7275; A61B 5/7278; A61B 5/02433; A61B 5/1455; A61B 5/14551; A61B 5/14552
See application file for complete search history.

(56) References Cited

U.S. PATENT DOCUMENTS

| | | | |
|---|---|---|---|
| 10,165,951 | B2 | 1/2019 | Sola i Caros et al. |
| 10,420,490 | B2 | 9/2019 | Rich et al. |
| 10,806,374 | B2 | 10/2020 | Inan et al. |
| 2008/0177189 | A1 | 7/2008 | Kim et al. |
| 2013/0324859 | A1* | 12/2013 | Park .................. A61B 5/02007 600/479 |
| 2014/0005557 | A1 | 1/2014 | Rich et al. |
| 2015/0112606 | A1* | 4/2015 | He ..................... A61B 5/02055 702/19 |
| 2016/0007862 | A1 | 1/2016 | Ku |
| 2017/0042435 | A1 | 2/2017 | Vermeulen et al. |
| 2019/0032833 | A1 | 10/2019 | Wijshoff et al. |
| 2019/0336081 | A1 | 11/2019 | LeBoeuf et al. |
| 2019/0350532 | A1 | 11/2019 | LeBoeuf et al. |
| 2020/0305738 | A1 | 10/2020 | Genicot et al. |
| 2021/0030290 | A1 | 2/2021 | Lee et al. |
| 2021/0052175 | A1 | 2/2021 | Stephens et al. |

FOREIGN PATENT DOCUMENTS

| | | |
|---|---|---|
| WO | WO2012/074193 | 6/2012 |
| WO | WO2020/176214 | 3/2020 |

OTHER PUBLICATIONS

Max Pulse Device webpage https://maxpulsedevice.com/ retrieved Feb. 15, 2024.
Long Life Cario webpage https://longlifecardio.com/max-pulse/ retrieved Feb. 15, 2024.
Manitoba Technology Accesserator webpage https://mbtechaccelerator.com/company_highlight/arterial-stiffness-inc/ retrieved Feb. 15, 2024.
510(k) No. K110374.
510(K) No. K200567.

* cited by examiner

HEMODYNAMIC DETERMINATION OF ARTERIAL STIFFNESS, ARTERIAL AGE, ARTERIAL DEPOSITS AND HBA1C

RELATED APPLICATIONS

The present invention is a Continuation in Part of U.S. Ser. No. 17/523,754, filed on 22 Dec. 2021. Additional patents or applications of related continuity are further disclosed as part of the Application Data Sheet filed pursuant to 37 C.F.R. § 1.76. All Related Applications are incorporated by reference as if fully rewritten herein.

BACKGROUND OF THE INVENTION

1. Field of the Invention

The present invention generally relates to systems for measuring glycated hemoglobin (HbA1c), arterial stiffness, arterial age, arterial deposits, and, more particularly, to a novel non-invasive pulse wave velocity detection device for use.

2. Description of the Related Art

Cardiovascular health problems caused directly or indirectly related to the cardiovascular system have been one of the significant global health concerns contributing majorly to the number of human deaths annually. Cardiovascular disease accounts for one of every three deaths in the United States and is the leading global death cause. Cardiovascular disease also carries an astronomical toll on the healthcare system worldwide, and in the United States, including billions of dollars in healthcare costs annually, tremendous use of healthcare resources, and overall morbidity to the general population. However, there are no effective ways currently in the market to screen and detect the early stages of coronary artery disease.

Current technology in cardiovascular disease cannot prevent vascular disease (including coronary and peripheral artery disease). However, it can detect and monitor comorbidities' damage to the cardiovascular system when they become severe and symptomatic. Prediction of cardiovascular disease in its early stages would thereby be incredibly beneficial.

Measuring pulse wave propagation offers a valuable screening and predictive tool for cardiovascular diseases. Pulse wave propagation can be described as an arterial wall disturbance caused by the ejection of blood from the heart that propagates mainly toward the periphery. Pulsewave Velocity ("PWV") and Arterial Stiffness Measurements are methods to measure regional arterial stiffness of the arterial territory between two measurement sites. These parameters are related not only to the elastic modulus of the arterial wall (which represents the intrinsic stiffness of the wall) but also to the arterial geometry (thickness and radius) and blood density.

Some methods and devices incorporate various mechanisms for measuring pulse wave propagation. For example, Meridian Co. Ltd of Korea provides the McPulse™ Digital Pulse Analyze, which uses a pulse oximeter to detect a pulse wave and take a "snapshot" of arterial elasticity that purports to be sensitive to early arterial changes that may be indicative of potential underlying vascular disease. A medical practitioner must use any changing results tracked over time, considering the potential effects of client-specific risk factors, for such an indication of arterial elasticity to be useful.

Arterial Stiffness Inc. of Canada also provides a device for measuring plaque levels in arteries. Such a system requires generating a library of analog pulse contours from the individual over time. It is highly dependent on possible variations in the position of the fingertip photoplethysmography device relative to the user's heart (level and extension of the arm).

Medicor Co. Ltd of Korea provides the MaxPulse™ System that measures blood oxygen saturation ($SpO_2$) and heart rate using a photoelectric plethysmograph. The main improvement of the MaxPulse™ system appears to be specific to the finger-type reusable sensor, where the LED generates red and infrared light about a 5 $mm^2$ photodiode active area of the patient's left index fingertip.

Cardiosense, Inc. of Chicago, IL utilizes a CardioTag™ wireless, wearable device to capture ballistocardiogram (BCG) data to assess cardiac function parameters. As described in U.S. Pat. No. 10,806,374, methodologies are identified for converting the wearable acceleration signals to BCG signals such that analysis and interpretation tools can be used for both measurements.

Also, several pulse oximeters marketed to consumers as fitness or wellness tools also exist. When used by laypersons, information concerning oxygen saturation may merely be used to inform the user concerning lifestyle/fitness decisions, such as, for example, verifying $O_2$ concentration for high altitude or other training.

Despite the many methods and devices for identifying PWV or measuring arterial stiffness, none of these current technologies have resulted in an affordable and accessible screening solution for detecting and monitoring the damage comorbidities have on the cardiovascular system in their early stages. Currently, available diagnostic tests are expensive and poorly suited for daily practice, and they do not serve a screening purpose effectively. Carotid ultrasonography is an ultrasound-based diagnostic imaging technique to evaluate the structural details of the two major blood vessels in the neck—the "carotid arteries." Pulsewave Technologies of Austin, Texas, provides a large and expensive device that uses the ankle-brachial index and pulse wave velocity methodology. Non-contrast enhanced computed tomography (CT), also called calcium score heart scan, is currently used to find calcium deposits in the arterial plaque of people with heart disease but has no role in screening and is mainly used to diagnose when a blockage is already 80-90%. Additionally, such testing imparts high radiation dosages to the patient and personnel. Coronary angiography is an invasive procedure that inserts a small tube into an arm vessel and threads through to the aorta and the heart to perform tests.

Consequently, there is an unmet need for practicing physicians to overcome high costs, equipment scarcity, the need for skilled personnel or specialists, or a lack of portability. Improvements are needed for the affordable detection and monitoring of cardiovascular diseases and the state of diabetes management to provide early intervention for disease management and regression.

SUMMARY OF THE INVENTION

It is thus a general object of the present invention to provide a system and device for rapid screening, detection, and monitoring of cardiovascular health and diabetes-related problems.

It is also a broad object of the present invention to allow for screening of elasticity of small and large arteries to provide healthcare practitioners with a comprehensive analysis and critical information regarding arterial stiffness and aging to determine the optimal treatment pathway.

The present invention's more specific object is to measure arterial stiffness and age, glycated hemoglobin (HbA1c), and arterial deposits.

Briefly described, the present invention comprises an advanced cardiovascular health monitoring system using an optical PPG pulse wave velocity detection device in combination with a software system for analyzing data waveforms of personalized patient data integration. The system enables non-invasive and continuous monitoring of arterial health, offering improved convenience to patients. Incorporating patient height and weight into calculations significantly improves the precision of cardiovascular assessments. This approach enhances the overall accuracy of our assessments, empowering the health practitioner. The captured data is then structured to identify at least one physiological parameter. Specific physiological parameters can be identified, including coronary stiffness, peripheral stiffness, carotid thickness, arterial deposits, aging index, pulse transit time, vascular index, stress index, stroke volume, HbA1c, heart rate, and heart rate variability, pulse signal, systolic and diastolic blood pressures, blood oxygen saturation, mean arterial pressure, cardiac output, and pulse pressures.

Analysis of structured data around these physiological parameters may further provide for the monitoring and assessment of specific health conditions, including diabetes, vascular assessment, arterial diseases, arterial compliance, arterial aging, venous assessment, endothelial functions, vasospastic conditions, autonomic function monitoring, vasomotor function and thermoregulation, orthostasis, and other cardiovascular variability assessments.

Further, the present invention determines a level of glycated hemoglobin, or hemoglobin A1c ("HbA1c"), through a non-invasive method.

Further still, the present invention identifies subclinical atherosclerosis through the determination of arterial stiffness and arterial age.

Even further still, the present invention may measure the amount of fatty buildup (soft and hard plaques containing calcium and other minerals) in the walls of the arteries that supply the heart muscle via the determination of arterial deposits.

According to one aspect of the present invention, a pulse wave velocity detection device is provided that comprises an integrated pulse detection component. The pulse detection component comprises a central control chip and a pulse acquisition unit for acquiring human pulse information. Having a smaller form factor and being more precise in pulse detection, the pulse acquisition unit provides user-friendly pulse wave data detection and captures in a non-invasive manner. Based on the different cycle methods combined with modeled Artificial Intelligence (AI) networks, various PPG features may be extracted and further developed or analyzed. Based on preset cardiovascular parameter functions, corresponding cardiovascular parameters of each cardiac cycle may be obtained. The device provides, along with its operation software, for monitoring the status of blood vessels by using several differential functions of the pulse wave and classifying types of blood vessel flow.

The optical finger-PPG sensing device with a biomedical sensing function may measure various bio-information through the pulse waves of blood vessels for determination based on various indices to estimate the risks of arteriosclerosis and stiffening of the arteries. Light intensity signals may be measured and used with time dynamics and analytics to evaluate the PPG signal changes for other related biomedical applications.

According to another aspect of the present invention, such a non-invasive sensor may be further adapted for deducing lipid and hormonal levels through light reflection and pulse wave analysis.

According to yet another aspect of the present invention, the development of such non-invasive sensors may be further adapted for the estimating of glucose levels directly through the measurement of oxygen saturation deduced through metabolic heat.

The advantages of the present invention allow for the acquisition of pulse waveforms, heart rate, blood pressure, and blood oxygen saturation that can be directly outputted for direct monitoring or further analysis.

The following description will reveal further objects, features, elements, and advantages of the invention.

BRIEF DESCRIPTION OF THE DRAWINGS

The advantages and features of the present invention will become better understood regarding the following more detailed description and claims taken in conjunction with the accompanying drawings, in which like elements are identified with symbols and in which:

DESCRIPTION OF THE PREFERRED EMBODIMENTS

The best mode for carrying out the invention is presented in terms of its preferred embodiment, herein depicted within the Figures and Tables.

1. DETAILED DESCRIPTION OF THE FIGURES

Figure 1:
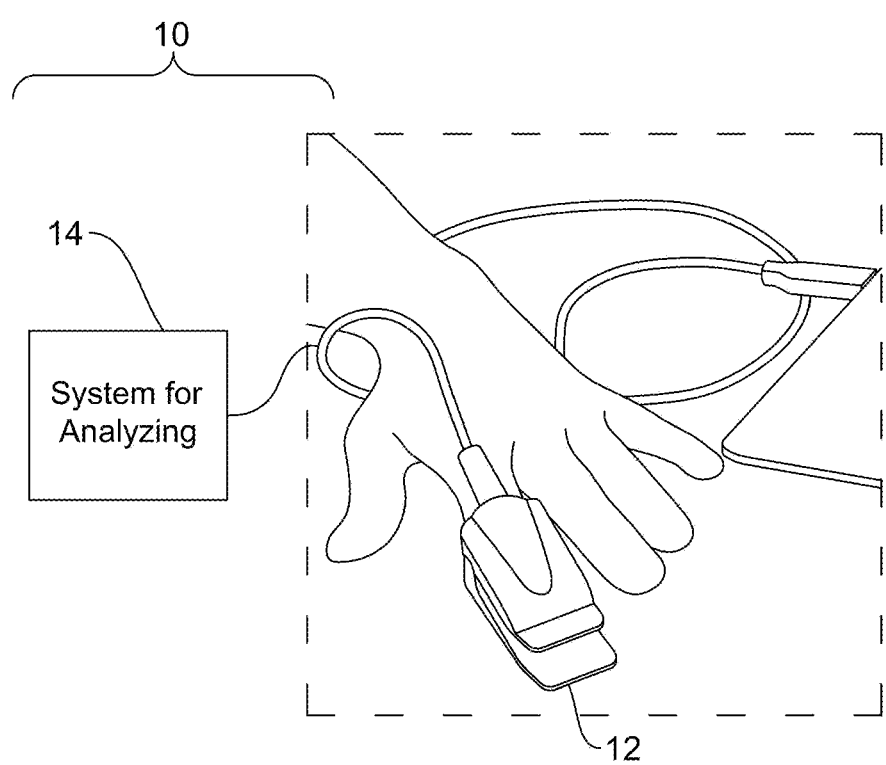
FIG. 1 is a block diagram of a non-invasive pulsewave velocity detection device structure according to the preferred embodiment of the present invention.

As shown throughout the Figures, where references identify elements, the present invention provides a device for and system of use in various disease screening methods through the identification of volumetric blood flow pulsation signals. As shown in conjunction with FIG. 1, the preferred embodiment of the present invention, generally denoted as 10, comprises a pulse wave velocity detection device 12 in combination with a system for analyzing data waveforms 14. The pulse wave velocity detection device 12 preferably comprises a pulse detection module having a compact and integrated form factor and more preferably comprises a finger-type PPG (optical) sensor device such as the embodied by the "QuanCardio™" finger-type Photoplethysmogram (PPG), an optical sensor device, as commercially provided by Quantum BioTek of Atlanta, GA and further disclosed in greater detail in the Related Applications and incorporated by reference as if fully rewritten herein. Detection device 14 provides a high-precision sensor for capturing arterial data, eliminating the need for cuff-based measurements.

Figure 2:
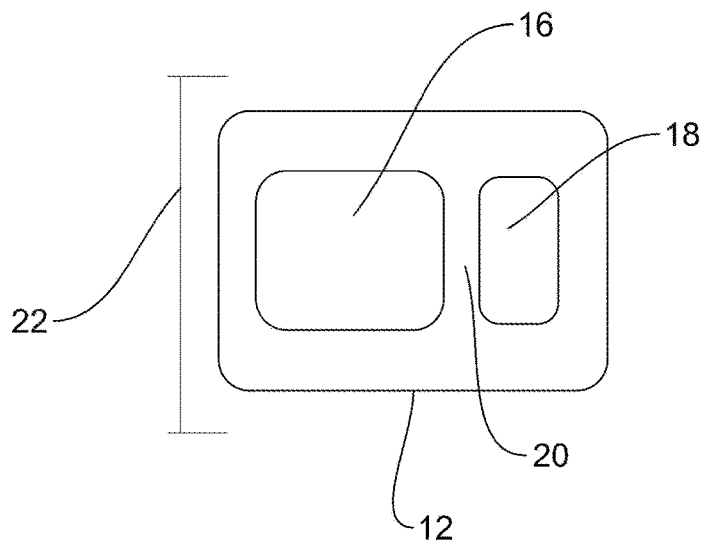
FIG. 2 is a schematic of the pulsewave velocity detection device 12 for use therewith.

As shown in conjunction with FIG. 2, the system for analyzing data waveforms 14 may be provided as a separate unit housed in operational and electronic communication with the pulse wave velocity detection device 12. The system for analyzing data waveforms 14 may further comprise a compact form factor integrated into a housing common with the pulse wave velocity detection device 12.

Figure 3:
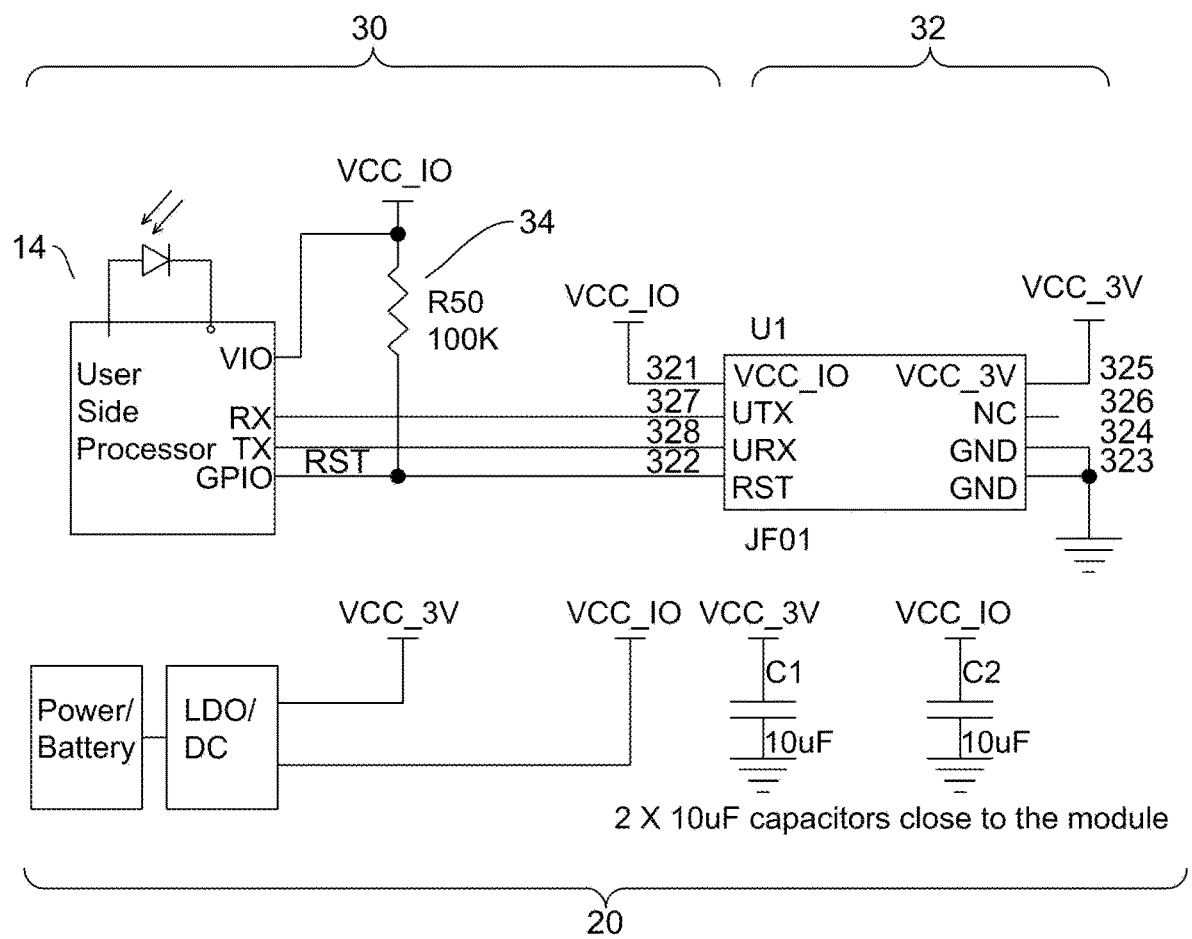
FIG. 3 is schematic of the system for analyzing data waveforms 14 for use therewith.
Figure 4:
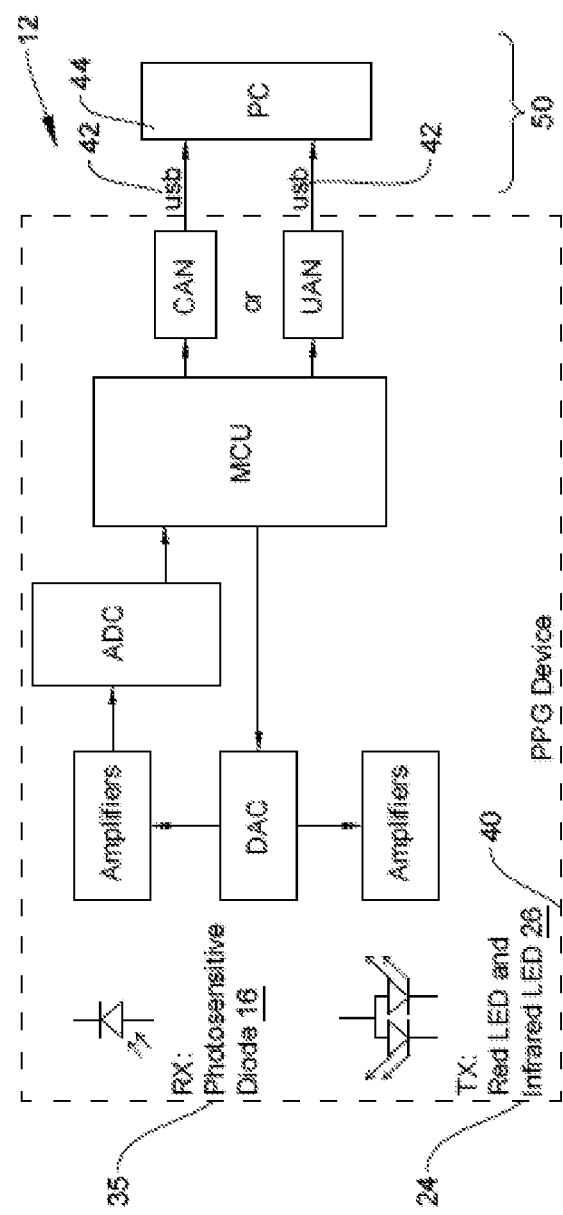
FIG. 4 is a schematic block diagram depicting the operation of the on-invasive pulsewave velocity detection device structure according to the preferred embodiment of the present invention.
Figure 5:
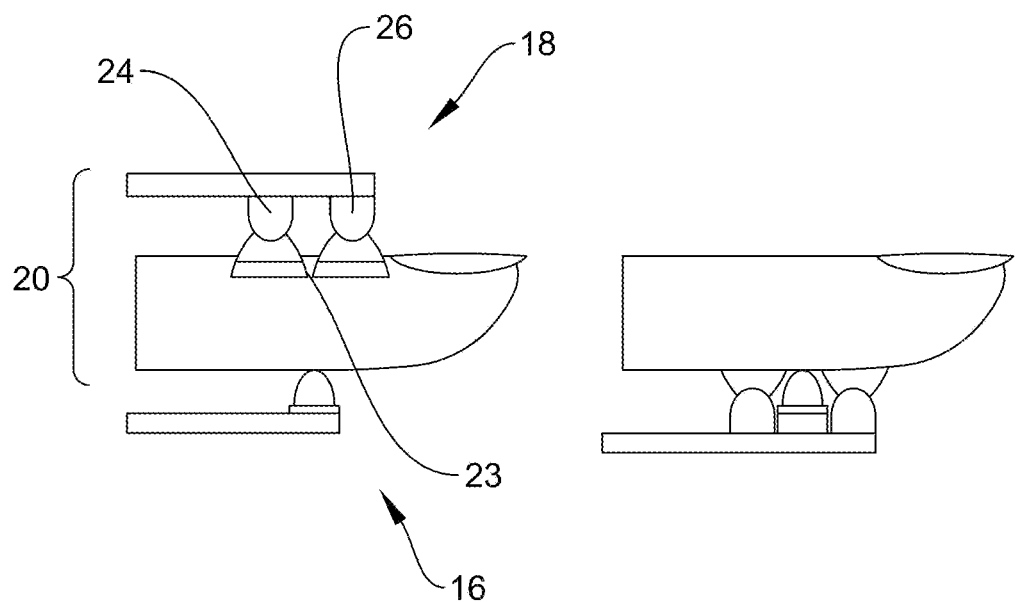
FIG. 5 is a schematic representation of sensor modes in a finger-type PPG sensor in accordance with the preferred embodiment of the present invention.

As best shown further in conjunction with FIG. 3 through FIG. 5, the pulse wave velocity detection device 12 may comprise a photodiode sensor ("sensor") 16 that is operatively controlling a light emitting diode ("LED") 18, with a spacer 20 separating the spacer 20 from the LED 18. The Spacer 20 may be black or opaque. It would preferably provide for non-transmission between the sensor 16 and the LED 18 to improve signal quality. Sensor 16, preferably, may comprise an integrated circuit. Within the housing of the pulse wave velocity detection device 12, the integrated circuit and LED 18 may be encased with a glass sheet 22. The glass sheet 22 is preferably adapted to protect the sensor 16 and a sensor projection area 23 that is preferably well-connected to red 24 and infrared 26 light transmission materials.

As best shown in conjunction with FIG. 3, a schematic of the integrated circuit is shown in which a central control chip 30 is in operational connection with pulse acquisition unit 32. Additional components are described in conjunction with Table 1, with the electrical performance best described in conjunction with Table 2.

TABLE 1

| Reference/Part number | Signal Name | Function | Specified Examples |
| --- | --- | --- | --- |
| 321 | VCC_IO | Digital IO power | 2.6 V~3.6 V |
| 322 | RESETn | The module is reset | Low level effective |
| 323 | GND | Power supply | |
| 324 | GND | Power supply | |
| 325 | VCC_3V | LED power supply | 2.9 V~5.5 V |
| 326 | NC | retain | Must be suspended |
| 327 | UTX | Module UART sends | The level is consistent with the VDD_IO |
| 328 | URX | Module UART receives | The level is consistent with the VDD_IO |

TABLE 2

| Signal name | Voltage Range |
| --- | --- |
| VCC_3V | −0.3 V~6 V |
| VCC_IO | −0.3 V~3.8 V |
| URX | −0.3 V~(VCC_IO + 0.3) V |
| RESETn | −0.3 V~(VCC_IO + 0.3) V |

Referring in conjunction with FIG. 4, a schematic block diagram depicting the operation of a device structure according to the preferred embodiment of the present invention. The pulse wave velocity detection device 12 includes an analog side 40 in communication with a digital side 50. The analog side 40 incorporates the optical module as a scanner that detects the data and generates the pulse wave at a specific baud rate. The digital side 50 controls the power and manages the pulse wave velocity detection device 12. Analog data generated is communication 42 to a computer 44 where data may be uploaded and sent to the algorithm software on the computer 44 that does the analysis. Computer 44 may also contain USB and driver software.

The pulse acquisition unit 32 further comprises a photosensitive assembly, and the photosensitive assembly comprises a photodiode 16 and a resistor 34. The resistor 34 is connected with the photodiode 35 in parallel, with two ends of the photodiode 35 connected with the central control chip. The working principle involves acquiring and processing collected signals, calculating physiological indexes such as heart rate, blood oxygen saturation, and blood pressure, and transmitting data waveforms through the universal asynchronous receiver transmitter ("UART") interface.

The pulse wave velocity detection device 12 of the present invention is thereby adapted for use as a piece of medical testing equipment, used mainly in cardiovascular chronic disease management and monitoring health abnormalities. One such preferred use includes providing a system and method for disease screening by identifying volumetric blood flow pulsation signals and correlating the same to monitor to detect the early stages of vascular disease. The device has been developed to function much more than a pulse oximeter that measures cardiovascular conditions and, used in conjunction with its related software, is designed as a preventive, pre-cursive indicator of cardiovascular health and events. While various uses may be identified by those having ordinary skill in the relevant art in light of the present teachings, the device is intended to be used in particular focus on basic cardiovascular flow parameters (heart rate, mean arterial pressures), pulse analyses (pulse wave velocity, pulse pressure indices) diabetes-related factors (glucose measurements and glycated hemoglobin, peripheral artery diseases), stress indicators, arterial age estimation (arterial stiffness indices), and vascular conditions (large and small arteries circulation and blockage).

The present invention allows preventative screening to be obtained using data from a dual-data collection micro biosensor that provides a platform that couples photoplethysmography PPG technology with artificial intelligence (AI). Sensors embedded in a finger probe capture pulse wave velocity to measure the status of heart and blood vessels, arterial wall stiffness, and biological age of arteries, among other factors. The present non-invasive medical device rapidly detects the different stages of cardiovascular disease and diabetes management by analyzing the subtle characteristics of the human body's volumetric blood flow pulsation signals. Additionally, non-invasive and rapid measurements of HbA1c (average blood sugar level over the last three months), arterial age, or arterial deposits can also be obtained.

Depending on the relative position between LED 24, 26, and PD 16, a photoplethysmography acquisition system may be used in reflection or transmission modes. As shown in conjunction with FIG. 5, reflection mode is called reflection mode when both optical elements are placed on the same surface and applied onto the measurement site (for example, upon the finger). The reflection mode, as shown, is where the light source and photodetector are placed in parallel, thereby allowing for the measurement of backscattered light from any skin surface. The intensity of light reaching the photodetector is measured, and the variations are amplified, filtered, and recorded as a voltage signal.

In the transmission mode, also shown in FIG. 5 and employed in the preferred configuration, optical elements are placed from either side of the measurement site (for example, across the finger).

When using photoplethysmography for pulse signal acquisition, motion artifacts are a central issue to be addressed, particularly in ambulatory conditions. For example, suppose a user is still and no motion is induced at the measurement site. In that case, photoplethysmographic signal frequencies represent cardiac activity and heart rate more. However, if the user engages in physical activity, especially ambulatory activity such as walking, running, or any other activity that can impart or imply motion on the measurement site, an unwanted noise on the PPG signal may be induced. Unfortunately, such noise has a spectral content that overlaps with the cardiac band and, thus, cannot be removed using conventional linear filtering techniques.

The amplitude of the volume pulsations with each heartbeat is correlated with the flow. In PPG, depending on the probe design, the volume under study can be 1 $cm^3$ for transmission mode systems. The Beer-Lambert law for light transmission in an absorbing medium, as shown in Equation (1), is the primary basis for the functioning of the photoplethysmograph:

$$I = I_0 e^{-(\mu_a d)} \tag{1}$$

where I is the transmitted intensity, $I_0$ is the input light intensity, $\mu_a$ is the absorption coefficient, and d is the distance between the source and detector.

Since blood is a highly scattering medium, Beer-Lambert's law must be modified to include an additive term G due to scattering losses and a multiplier B to account for the increased optical path length due to scattering and absorption. The modified Beer Lambert's law, which incorporates these two additions, is shown in Equation (2):

$$I = I_0 e^{-(\mu_a dB + G)} \tag{2}$$

This approach helps to understand the absorbencies of light as it passes through living tissues and the mechanism of PPG, where G is a factor dependent upon the tissue's measurement geometry and scattering coefficient. The wavelength of the source used is of significant importance in PPG. Light sources that operate in the near red (600-700 nm) and near-infrared (880-940 nm) spectrum are most preferred as effective because the whole blood has a relatively small absorption at wavelengths greater than 620 nm.

Figure 16:
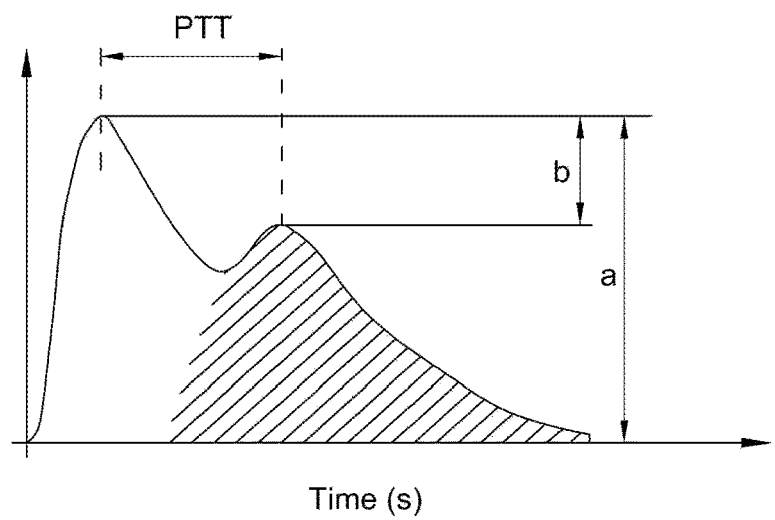
FIG. 16 is a graphical representation of a PPG signal denoting the PPG peaks.

As shown in conjunction with FIG. 6 and FIG. 16, PPG signals typically exhibit an early systolic peak and a later peak or inflection point that occurs a short time (t) after the first peak in early diastole. The first peak is formed mainly by pressure transmitted along a direct path from the left ventricle to the finger or measuring site (where it generates a change in blood volume). The second peak is partly formed by pressure transmitted along the aorta and large arteries to sites of impedance mismatch in the lower body, where it is reflected up the aorta. It can thus be used to infer the transit time taken for pressure to propagate along the aorta and large arteries to the significant sites of reflection in the lower body and back to the root of the subclavian artery.

Figure 6:
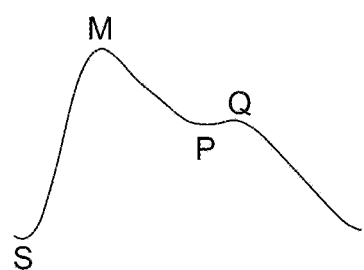
FIG. 6 depicts a representative PPG signal and its characteristic points.

The finger-type PPG signal reflects the blood movement in the vessel, which goes from the center (heart) to the end (fingertips) in a wave-like motion, as shown in FIG. 6, wherein M is the Systolic peak, S is the rise point, P is the Systolic notch and Q is the Diastolic peak. The signal may be affected by the heartbeat, hemodynamics, and the physiological condition caused by the change in the properties of an arteriole. These effects can be observed as distortions in the wave profiles. It is preferred that analyzing the PPG waveform may be used in circulatory and respiratory monitoring.

Two phases of the signal may be distinguished in an AC-PPG pulse: the anacrotic phase between points S and M, corresponding to the rising edge of the pulse and mainly related to systole, and the catacrotic phase between points M, P, and Q, corresponding to the falling edge of the pulse and related to the diastole and wave reflections from the periphery. A dicrotic notch is usually observed in the catacrotic phase.

It is further intended that similar modification and improvement in the simplified model of light behavior developed based on the Beer-Lambert law may provide new possibilities in interpreting the PPG wave, including identifying many smaller components superimposed into the PPG signal and its resulting wave. Identifying such smaller components may be intended as indicative of the cooperation of circulatory, respiratory, and autonomic systems and their influence on arterial and venous blood flow.

A multitude of factors affecting the blood flow and factors variable individually (such as the different thickness of the finger, skin color, and subcutaneous fat content) can cause many difficulties in reading and interpreting the PPG wave. An example is that there is no known method of PPG calibration, which means that one cannot compare the absolute numbers received by different people. It is impossible to set one reference point.

Figure 7:
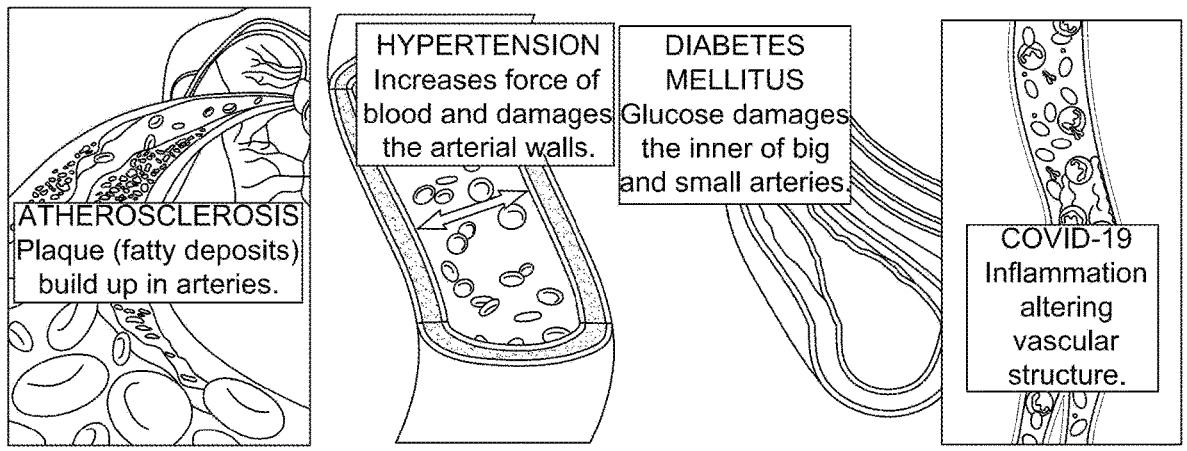
FIG. 7 is a pictograph indicating preferred focus areas for use with the present invention.

The present improved technologies of photoplethysmography (PPG) may thereby be used in various fields of medicine and clinical studies, such as the monitoring of physiological parameters, levels of oxygen saturation in the blood, cardiac output, heart rate, and its variability, blood and pulse pressures, respiration, lung capacity, vascular assessment, arterial diseases, arterial compliance and aging, venous assessment, endothelial functions, vasospastic conditions, autonomic function monitoring, vasomotor function and thermoregulation, orthostasis, and other cardiovascular variability assessments. However, with the main focus on the cardiovascular system, the present invention focuses primarily on those areas, as shown in FIG. 7, with a particular focus on the indicators and measurement of parameters to aid in the detection of atherosclerosis by measuring cholesterol levels and stiffness index. Further focus on hypertension may also be achieved by measuring basic cardiovascular parameters such as heart rate, blood pressure, and pulse pressure. Further still, the severity of glucose-related diseases and adverse effects on peripheral blood vessels may also be measured with HbA1c and PAD indicators being identified.

Using the finger type (clip) PPG technology, the present invention provides the platform to detect arterial stiffness (including coronary and peripheral stiffness), carotid thickness, aging index, arterial deposits, pulse transit time, vascular index, stress index, stroke volume, heart rate and heart rate variability, pulse signal, systolic blood pressure, diastolic blood pressure, blood oxygen saturation, mean arterial pressure, levels of oxygen saturation in the blood, cardiac output, blood pressures, and pulse pressures, respiration and lung capacity using cloud-computing, an advanced algorithm with artificial intelligence to provide the clinician with data and analysis to aid in treatment decisions. In order to accomplish such various early indicators, the PPG wave signal may be processed to reveal the condition of the circulatory (vascular) system, especially the arterial system. By analyzing the subtle characteristics of the volumetric blood flow pulsation signals of the human body, an arterial stiffness index ("SI") is determined by identifying the conduction time difference between the incident wave and the reflected wave (Ax Index).

A software interface is provided to accomplish this, forming a computer-based PPG analyzer. The signal is first obtained by infrared light through the finger. This signal is then converted into the digital domain by a signal processing circuitry containing amplifying and filtering steps, a microcontroller, and an analog-to-digital converter for display and further analysis.

While other measurements may be obtained, three primary forms may be obtained to estimate a depiction of current health conditions and as an indicator for predicting future cardiovascular risks and events. Blood flow analysis records and measures the flood of blow in the blood vessels from the changes in the direct relation of light absorption or blood flow changes. Blood volume pulse sensing deals with the PPG signal and the basic parameters deduced from the PPG wave. Digital Pulse Wave Analysis estimates and assesses how the walls of the arteries expand and relax when the heart beats, and the blood travels through the arteries, and other derivative information from the original PPG wave. Signal analysis techniques may be used to estimate cardiovascular parameters such as Basic Cardio-related Parameters; Pulse Wave Velocity; Pulse Wave Analysis; Pulse Transit Time; Pulse Pressure Index; Arterial Conditions, Vascular Health, and Stiffness Index; Estimated Arterial Age; Diabetes (HbA1c).

Basic Cardio-Related Parameters. Basic heart-related parameters may indicate general vascular health, risk of arteriosclerosis, and other cardiovascular and heart-related diseases. Such parameters include; heart rate, pulse signal, blood pressure (systolic and diastolic), blood oxygen saturation, and mean arterial pressure and microcirculation within small vessels.

Pulse Wave Velocity. Pulse wave velocity is the speed at which the blood pressure pulse propagates an artery or a combined length of arteries.

The pulse wave velocity may be obtained by segmenting the PPG signal from the device with noise-signal cancellation methods for accuracy and reproducibility into parts with various problems of capped data (wave distortion) solved with the averaging technique, a model fitting to optimize. Further methods and development of the Pulse Wave Velocity will be to model and predict a general equation of a PPG signal wave based on an age group, race, and gender types for an average person used as a standard for measurement. Both the Wavelength and the Pulse Transit Time are needed to derive the Pulse Wave Velocity. Several pulse wave velocities exist, such as; normal or arterial, aortic, branchial, carotid, the ankle, the toe, the femoral, and the blood pulse wave. These different types evolve as the heart muscles contract and retract to various parts of the body. However, one or a combination of these pulse waves is used for different devices.

Figure 8:
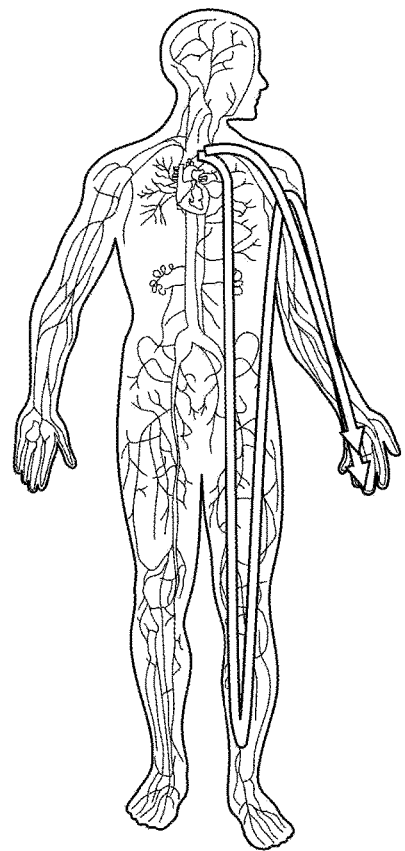
FIG. 8 is a schematic of a Forward-Wave and Retro-wave for Pulse Wave.

As shown best in conjunction with FIG. 8, according to one aspect of the present invention, a double system of a wave and retro-wave are incorporated to create a superimposed pulse wave that may be referred to as a heart-finger and heart-toe-finger paths, or a carotid-femoral pulse wave structure. Several approaches may be used to determine the Wavelength of a Pulse Wave, such as the Peak, Delay, Notch, and Maximum Slope methods. As shown best in conjunction with FIG. 9 and FIG. 10, these methods may incorporate the following data points:

A and A'=Starting points of the Pulse Waves (Foot of the wave);
B and B'=Pre-defined point of the Pulse Waves;
C and C'=Highest peaks of the Pulse Waves (Systolic Peaks);

D and D'=Second rise (peak) of the Pulse Waves (Diastolic Peaks);

E and E'=Systolic Notches; and

F and F'=Dicrotic Notches.

Figure 9:
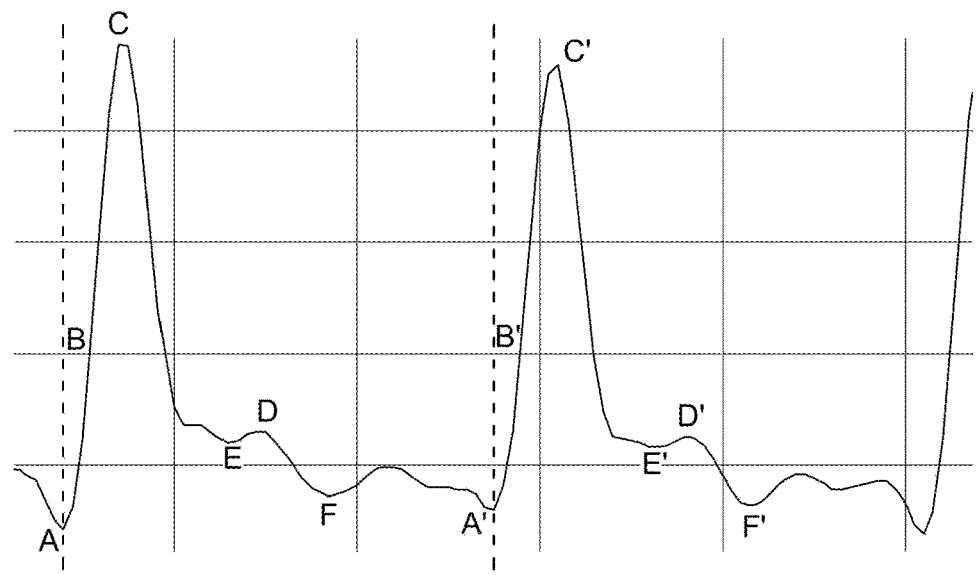
FIG. 9 is a graphical representation of a Pulse Wave Structure according to the preferred embodiment of the present invention.
Figure 10:
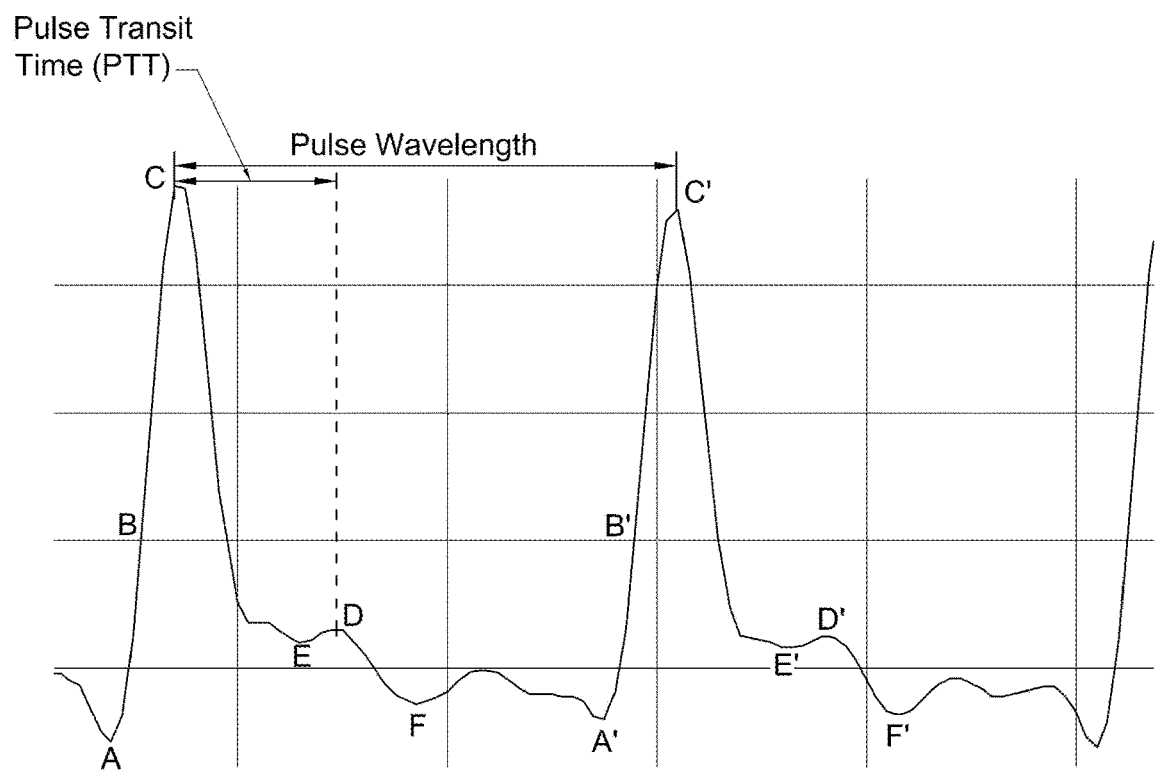
FIG. 10 is a graphical representation of a Pulse Wave Velocity Determination according to the preferred embodiment of the present invention.

Generally, the distance between any point defined on one part of the wave to the same point recurring on the wave is considered the wavelength. For the Peak Method, the distances between the systolic peaks (C and C'), as shown in FIG. 9, or between the diastolic peaks (D and D') are considered the Pulse Wavelength. Signal conditioning algorithms may be incorporated using such a method, precisely the Systolic peak-to-peak intervals. For the Delay Method, the distance from the starting points (A and A'), as shown in FIG. 9, is considered the wavelength of the pulse wave, with the dotted lines sectioning a complete, single pulse wave. This method is called the delay method because there is usually a time delay in the recurrence of the start point between successive intervals of the wave. The compensated time delay is usually used in pulse-time calculations.

The Notch method for wavelength determination utilizes the distances between two successive systolic notches (E and E') or dicrotic notches (F and F'). The presence or absence of especially the dicrotic notch makes this method not very comprehensive and inaccurate. The maximum slope method is usually used for pre-defined points on the pulse wave where the second derivative of the wave function is equal to zero. In the preferred embodiment of the present invention, some techniques may be used to measure and ensure accuracy, stability, and precision, as well as error estimation in the reading of Pulse Wave Velocity values using Averaging and Segmenting Methods. The Averaging method used in the beginning stages of development considered the final reading of the PWV value as the average of all systolic peaks. Due to noise, this method was further advanced into the Segmenting method. The segmenting method, however, incorporates other methods such as Time-Filtering Stabilization, Fitting and Modelling, and the averaging method. The time stabilization methods allow a few seconds where the data recorded is filtered out due to fluctuations caused by noise and to stabilize the range of reading. This method also brings problems as data seem capped, and very high values distort the readings. To solve the data capping problems, the model was redesigned and fitted with the pulse wave, segmented into single parts, and then wavelengths and pulse times determined. The individual pulse wave velocities were then averaged.

Figure 11:
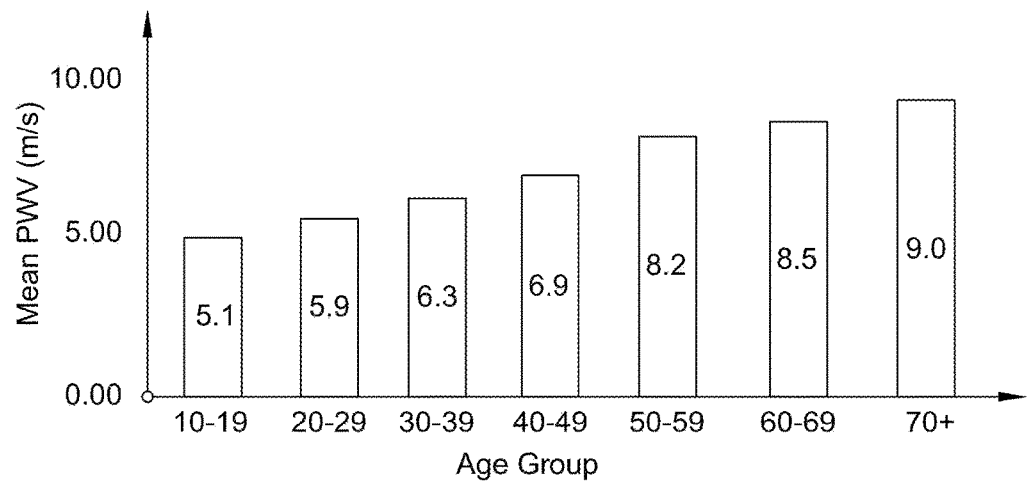
FIG. 11 is a bar graph showing Average Reference PWV Values.

Algorithms for Wavelength may determine the distance between point C to C', and for Pulse Transit Time, the wave travels from the Systolic to the Diastolic peaks (from C to D). After preliminary tests, average reference PWV values, as shown in FIG. 11, compared with QuanCardio PWV, produced the results as shown in FIG. 12.

Pulse Wave Analysis. The fluctuations observed in the original PPG, as shown in FIG. 11, are influenced by arterial and venous blood flow and the peripheral circulation's autonomic and respiratory systems. Such information could be used more comprehensively for phenotyping cardiovascular health. Due to increasing healthcare costs, a single sensor from which multiple clinical data points can be derived has become very attractive financially.

Figure 12:
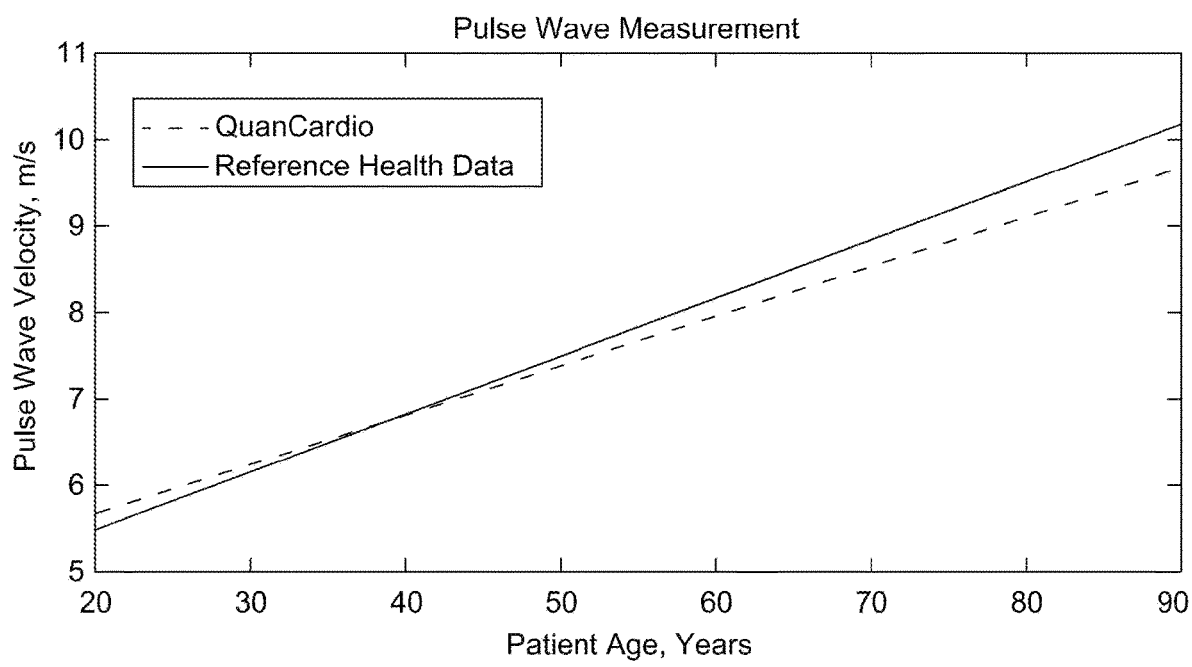
FIG. 12 is a chart depicting Pulse Wave Velocity Trends.
Figure 13:
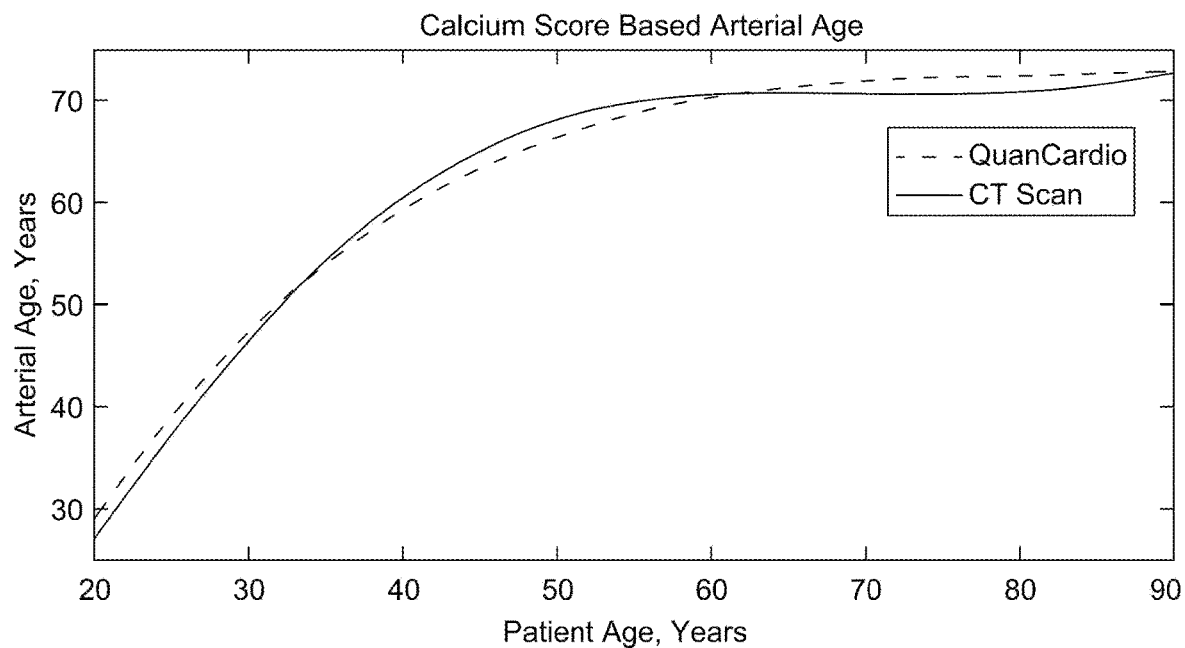
FIG. 13 is a graphical representation of Arterial Deposits (Calcium Score) Trends.
Figure 14:
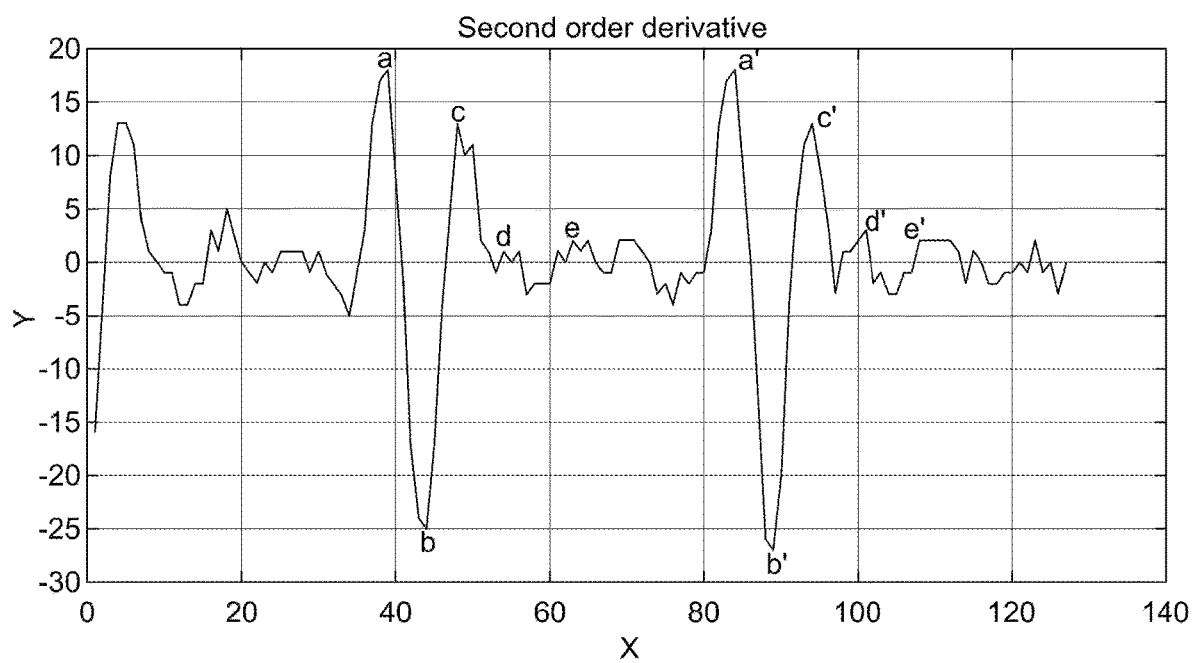
FIG. 14 is a graphical representation of a Second Derivative of a PPG signal with notations.
Figure 15:
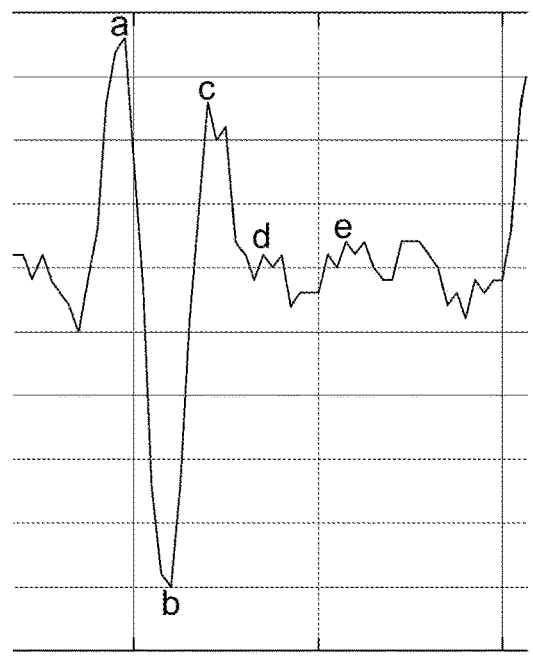
FIG. 15 is a graphical representation of a Segmented Second Derivative of a PPG wave.

As shown in conjunction with FIGS. 12, 13, and 14, various feature points of a Second Derivative PPG (DPPG) and Segmented Second derivative PPG (SDPPG) are also beneficial. Four (4) key feature points include:

Point a, the first extreme point of a PPG cycle, which is used to divide the whole signal into small cycles and PTT calculations;

Point b, the first minimal point of the PPG cycle, and used to calculate the AGI;

Point c, the second extreme point of the PPG cycle, and used for PTT calculations and RI calculations; and Point d is the PPG cycle's second minimal point used for the AGI calculation.

A wave-point algorithm may focus on the points on the wave and its derivatives for the determination of AGI and other parameters.

In many pulse wave applications, the path length of the wave is unknown. However, it can be assumed to be proportional to the subject height (h). The diastolic peak or inflection point is the point at which the first-time derivative of the wave (dPPG/dt) is closest to zero. The diastolic peak occurs when dPPG/dt is zero, whereas an inflection point occurs when dPPG/dt approaches zero.

The analysis of PPG images is used to extract the mathematical information of the four points, a, b, c, and d. The first and second derivatives method was used to calculate further information from the PPG wave. DPPG is the first-order derivative of the PPG image, and a zero value of DPPG means that there are extreme points in the PPG image. SDPPG is the second-order derivative of the PPG image. Also, it is the first-order derivative of the DPPG image. If the value of DPPG is zero and the value of SDPPG is negative, then the PPG image has extreme value points. If the value of DPPG is zero and the value of SDPPG is positive, then the PPG image has a minimal value point. Both SDPPG and DPPG are auxiliary tools used to analyze PPG images. It is a tool used to analyze the properties of the PPG signal.

Figure 17:
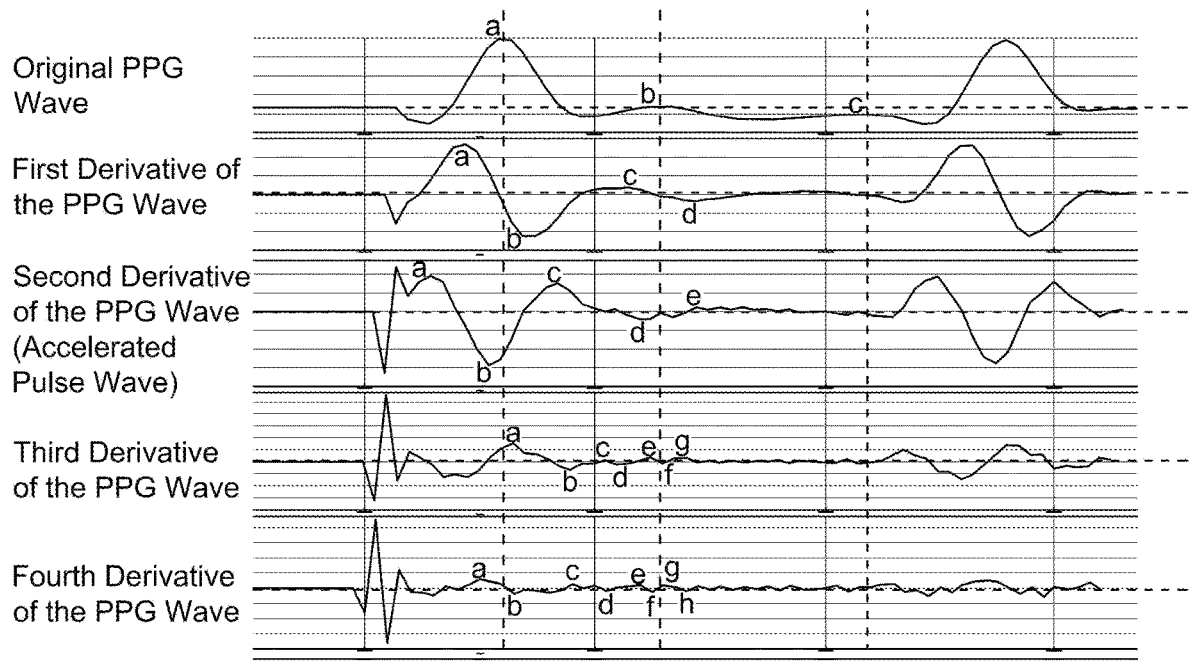
FIG. 17 is a graphical representation of the PPG waveform and its derivatives.
Figure 18:
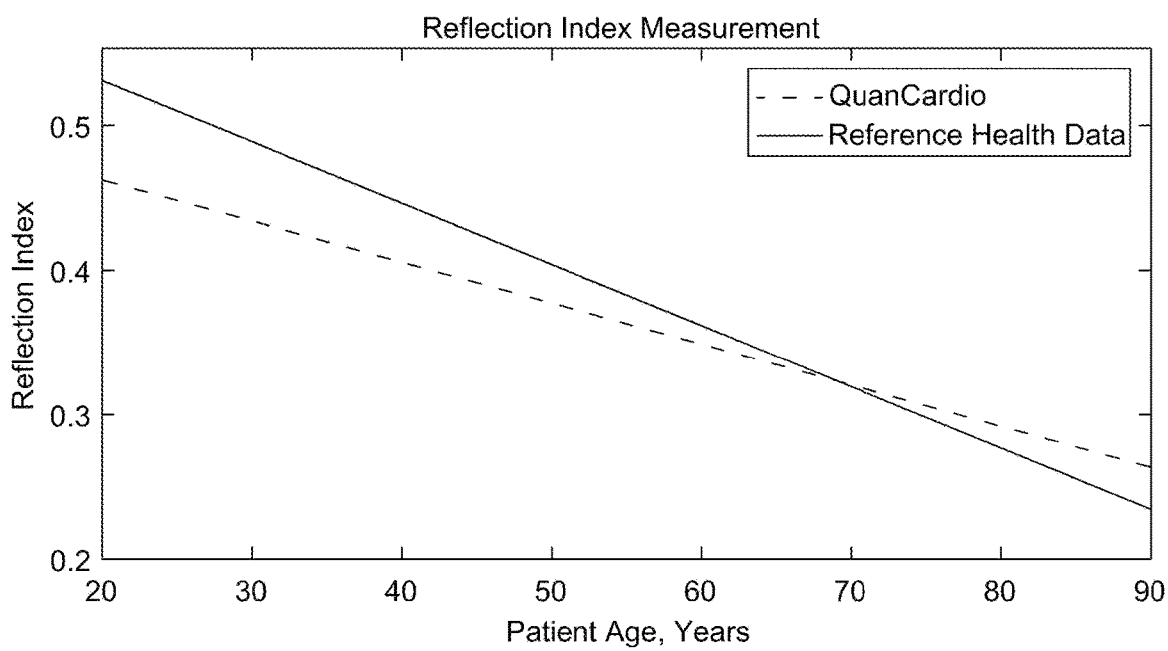
FIG. 18 is a graphical representation of a Reflection Index (Retro-wave) Trends.
Figure 19:
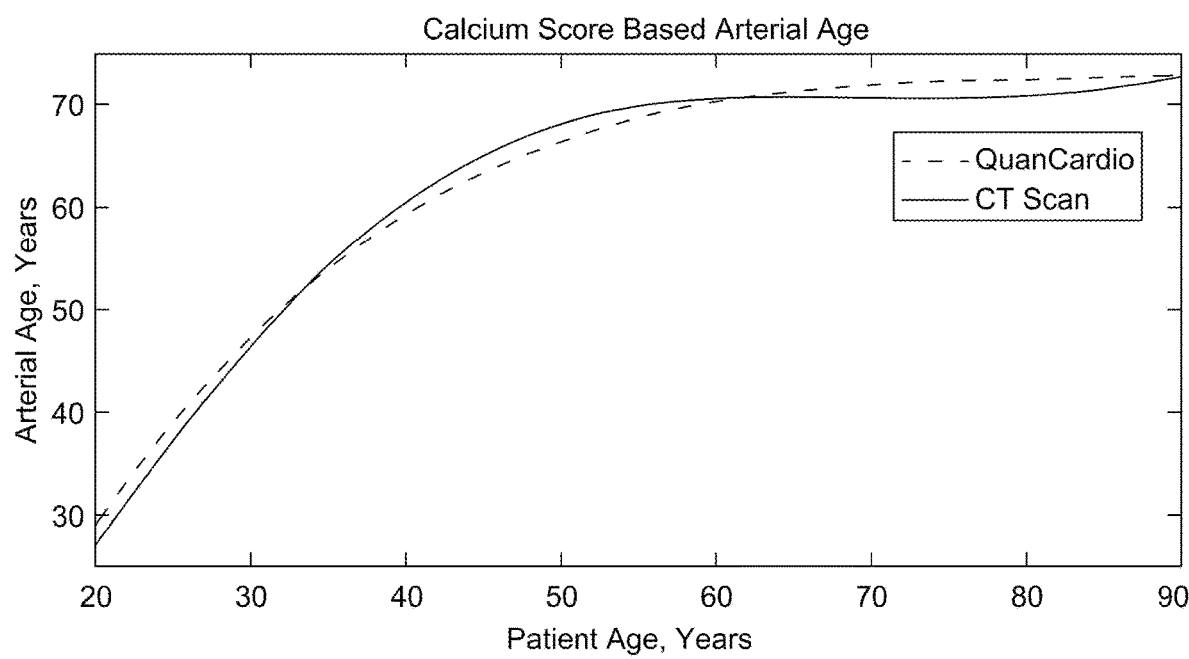
FIG. 19 is a graphical representation of Arterial Deposits (CAC score) trends based upon arterial age.
Figure 20:
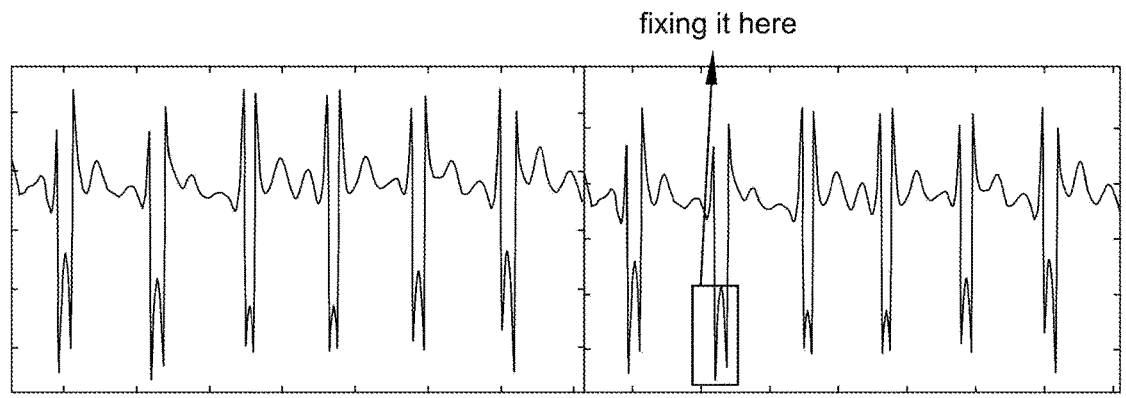
FIG. 20 is a graphical representation of a Cut-Off Low Values Points for use therewith.
Figure 21:
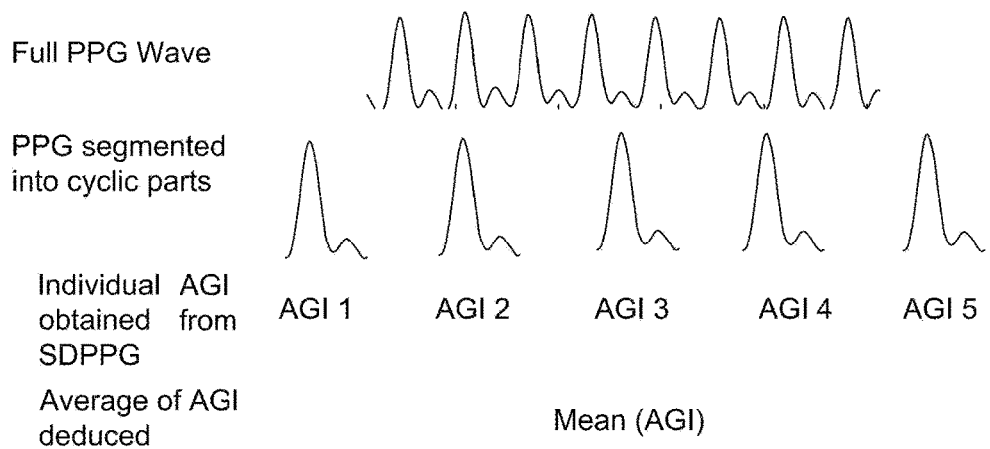
FIG. 21 is a schematic showing a Calculation method of Aging Index (AGI) and other parameters for use therewith.
Figure 22:
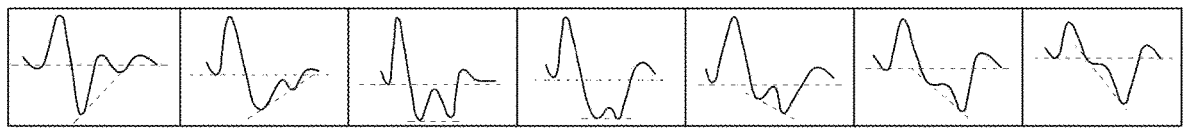
FIG. 22 is a schematic depicting a Sloping Method for Aging Index (AGI) calculation for use therewith.
Figure 23:
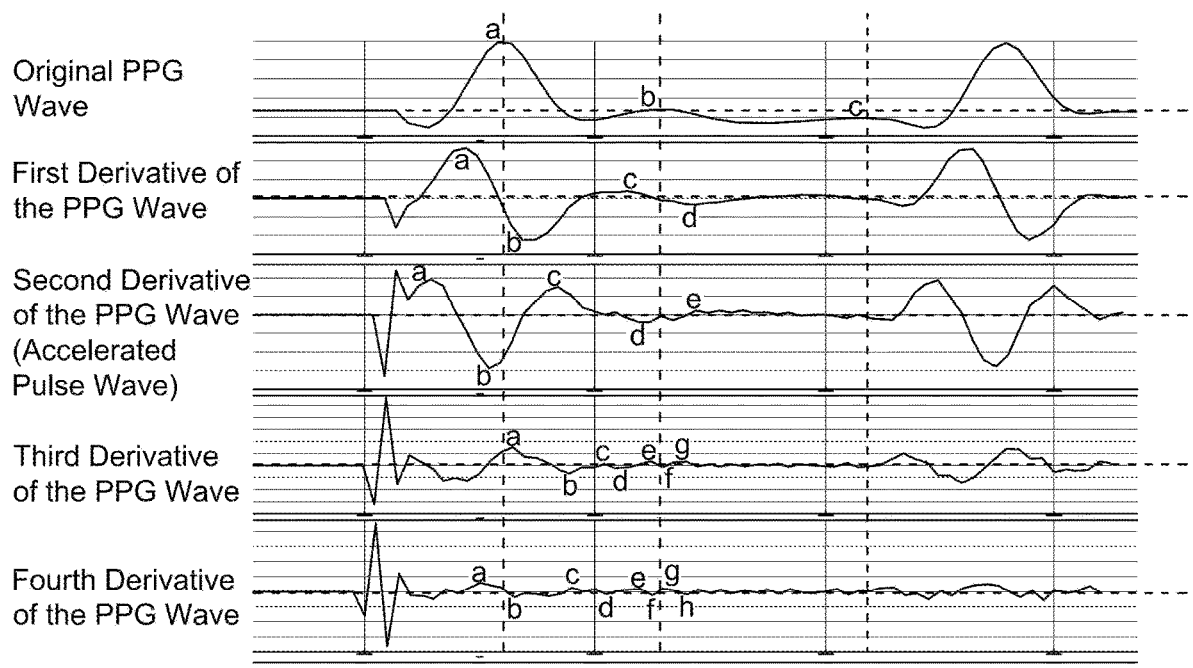
FIG. 23 is intentionally absent.
Figure 24:
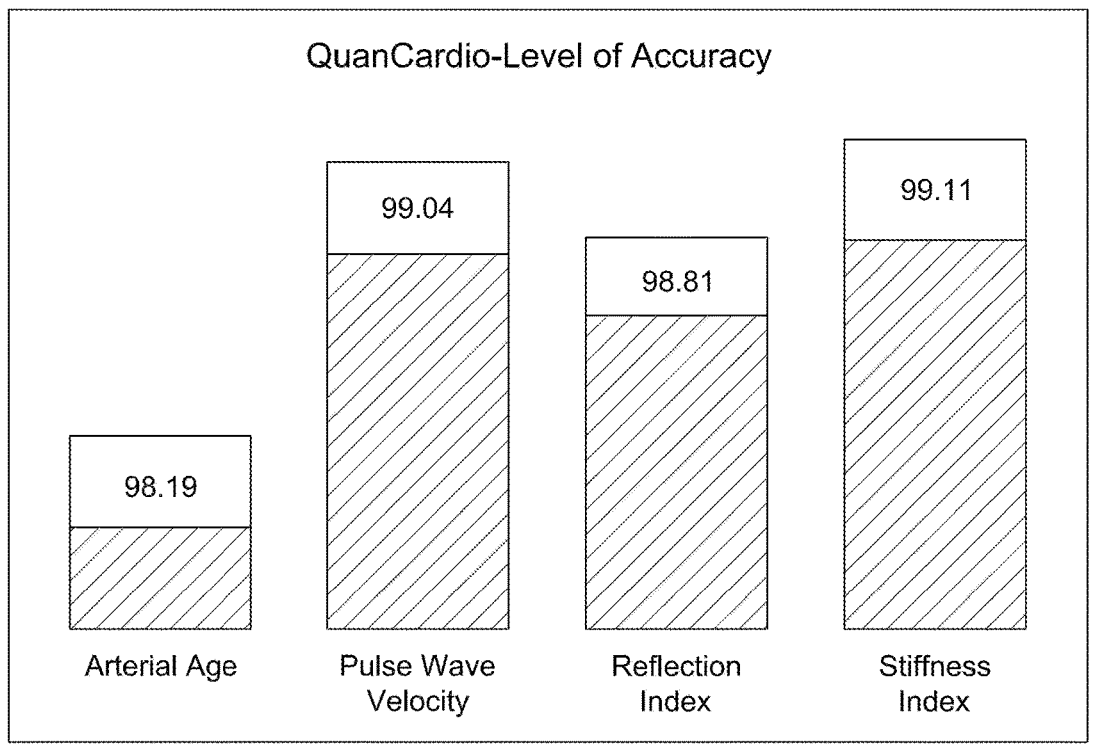
FIG. 24 is a bar chart showing Preliminary Correlation (Accuracy) Results of QuanCardio Testing.

Analysis of the waveform and its derivatives, as best shown in conjunction with FIG. 17, provides four separate systole waves (named a-d), and a diastole wave (named e) may be obtained. The a and b waves on the second derivative of PPG are included in the early systolic phase of the PPG. In contrast, the late systolic phase includes the c and d waves. The height of each wave from the baseline was measured, and their ratios b/a, c/a, d/a, and e/a were calculated.

Pulse Transit Time. Pulse Transit Time measures the time it takes for the heart pulse wave to travel throughout your body (heart to the left index finger, heart to the legs, and then to the left finger in a retro-wave, for the present invention) as shown best in conjunction with FIGS. 10 and 11, using successive local minima of curve algorithm methods of pulse transit time determination where the time it takes for the PPG signal to rise (or the foot of the wave) is used as the reference point of measurement. Pulse Transit Time in terms of accuracy was well-calibrated based on the various algorithms used in QuanCardio for pulse wavelength determination. Hence, there is no need to incorporate delay factors that may occur in other measuring methods, such as the brachial-ankle method of Pulse Wave Velocity determination.

Pulse Pressure Index. Despite the standard blood pressure measurement (systolic and diastolic), a more accurate and reliable index of the mean arterial pressure is used. The pulse pressure is also further optimized to a Pulse Pressure Index (PPI). As shown in conjunction with FIG. 11, a Reflection Index and its trends indicate peripheral arterial stiffness and vascular tone of small arteries. The RI index is calculated as the ratio of PPG's second wave peak to its first wave peak amplitudes. The Reflection Index (RI) is derived as a pulse inflection peak amplitude (second peak) ratio over the pulse max amplitude, as shown in FIG. 11 and Equation (3):

$$RI = b/a \qquad (3)$$

where RI can provide a window to vascular age and arterial compliance. RI mainly depends on detecting PPG second peak, which tends to be less pronounced with aging. The systole, diastole, and dicrotic notch points over the PPG contour may also be located and calculated by an optimized algorithm.

The measure of the vascular tone of the small arteries is known as the Reflection Index or RI. Influences that cause variations in RI can be as simple as the effect of caffeine or exercise.

Arterial Conditions, Vascular Health, and Stiffness Index. The present invention may estimate various conditions of the arteries, such as the Stiffness index, and other related indices for vascular such as the Aging Index (AGI), and the buildup of mineral fat deposits causing the blockage and deposits in the arteries.

The Arterial Deposit Score (ADS) estimates the development of soft and hard plaque, primarily caused by calcium and mineral deposits. This marker is employed to screen individuals at risk for coronary artery disease, even if they do not exhibit symptoms yet. ADS focuses on actively detecting arterial deposits, including hard plaque and calcium deposits, which are significant indicators of atherosclerosis. This advanced approach allows us to identify potential cardiovascular issues early, creating the opportunity for timely interventions and preventive measures. We actively optimize and calculate the ADS through extensive preliminary testing based on its various relationships with Pulse Wave Velocity (PWV) and other cardiovascular parameters.

Estimated Arterial Age. Based on various parameters optimized, estimates of the age of the arteries were deducted. The information from the derivatives of the original PPG wave was further used to analyze the age conditions of the arteries and other blood vessels. The Aging Index Value, one of the parameters used, represents the age of the arteries and other cardiovascular vessels. This parameter was calculated with Equations (4) and (5), and the measuring process is shown in FIG. 12 through FIG. 17:

$$AGI=(b-c-d-c)/a \quad (4);$$

and $$AGI=(b-e)/a \quad (5)$$

Diabetes. The HbA1c value may be determined based on the shape of the PPG signal, with an emphasis on the dicrotic notch. The b/a index is used in the estimation of a patient's diabetic conditions or Peripheral Artery Disease (PAD) conditions, and also the impact of other cardiovascular diseases such as COVID-19 and recovery, sugar, and fat buildup (cholesterol) on general health.

Figure 25:
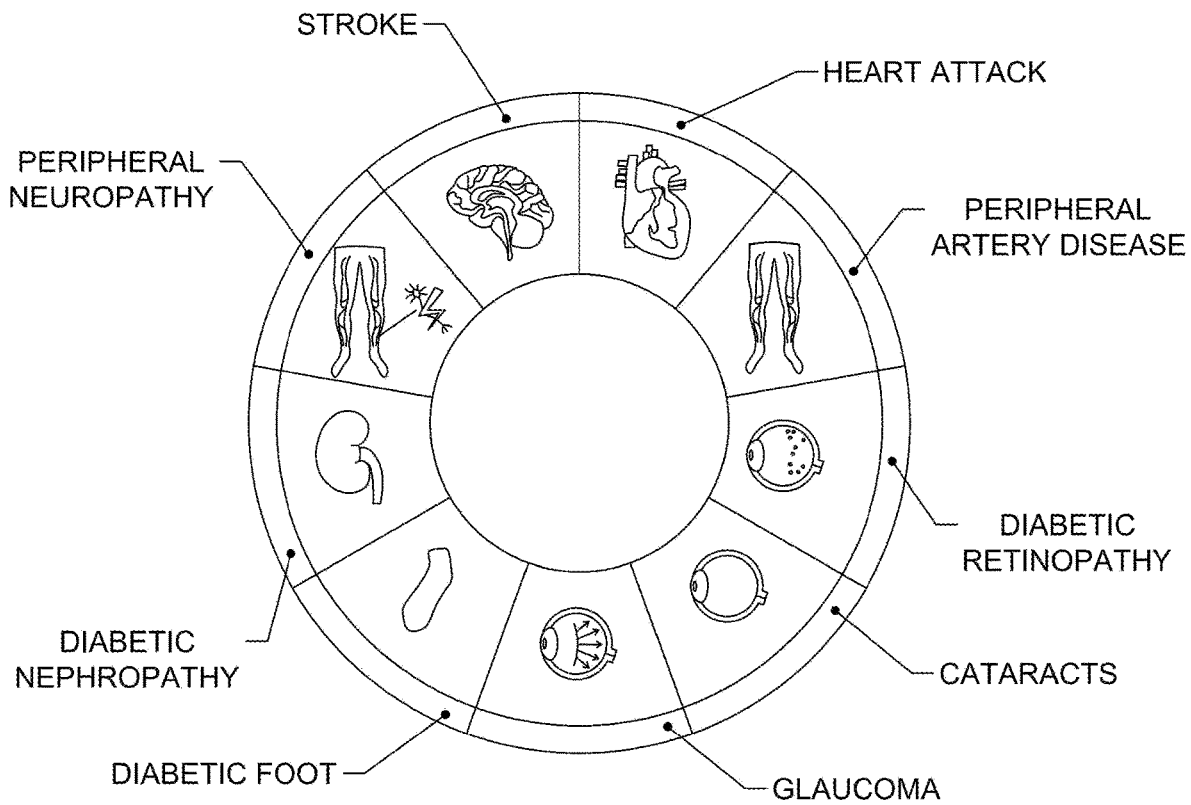
FIG. 25 is a pictograph showing Complications Related to Diabetes.

Diabetic patients are most prone to stroke and heart attacks, and those other conditions are shown in conjunction with FIG. 25. In most cases, high blood pressure is a pre-indicator condition for diabetes. Diabetes or an upsurge of blood sugar levels hinders the balance between vasodilation and vasoconstriction by reducing levels of Nitrogen oxide as well as other agents in the blood, and this causes different elasticities within the blood vessel. The endothelium, or lining of the arteries, gets destroyed eventually with time, and the plaque buildup within the arteries causes a hardening of the arteries (arteriosclerosis).

Blood pressure is strongly related to PWV. Harder (stiffer) arteries will exhibit a different PPG morphology than normal or high elastic arteries. Hence, the arterial stiffness indices and PWV of diabetic patients can be used as a parameter to measure diabetic-related diseases and applied to Peripheral Artery Disease. Further, using PPG may have additional applications in assessing blood circulation in patients with diabetes. Diabetes is a disease that can cause complications for virtually any system. Particularly destructive change in macro- and microcirculation significantly reduces patients' quality of life and increases their mortality. Many studies have confirmed the utility of PPG as a simple test to assess peripheral circulation in patients without systemic diseases. However, the use of this method in patients with diabetes and vascular complications may be significantly impeded.

Figure 26:
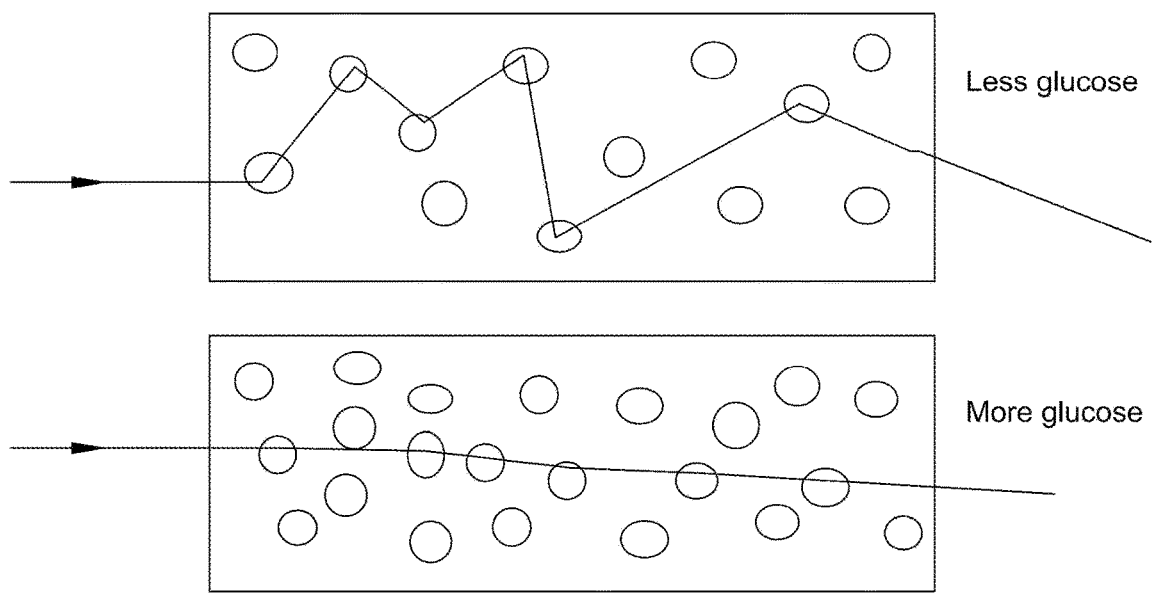
FIG. 26 us a Schematic Description of Glucose on Light Propagation.

In addition, researchers indicate that PPG may be a reliable tool for the assessment of disorders in microcirculation in patients with type 2 diabetes, wherein levels of blood glucose affect light propagation in a discernable manner. As shown in conjunction with FIG. 26, PPG pulse amplitudes can be used to assess microcirculation in people with type 2 diabetes. The b/a index represents the ratio of PPG's second derivative, b value, to PPG's second derivative, a value. (SDPPG) as shown in Equation (6). This index indicates the risk of occurrence of atherosclerosis and other cardiovascular diseases.

$$b/a\_index=b/a \quad (6).$$

Glycated hemoglobin (HbA1c) is the average blood glucose (sugar) level, usually within a period between the last three months. It gives the probability of developing diabetes complications with the eyes and feet.

2. OPERATION OF THE PRESENT INVENTION

Figure 27:
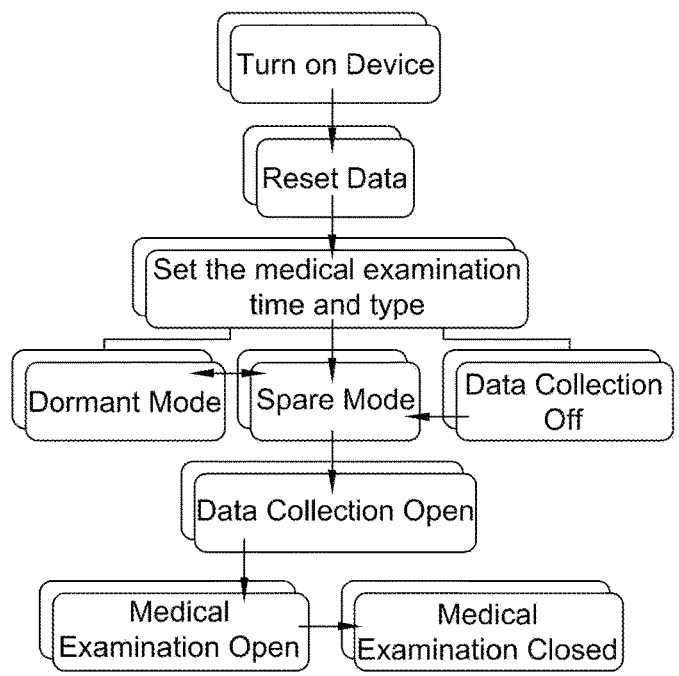
FIG. 27 is a communication flowchart for a typical and exemplary operation of the preferred embodiment of the present invention.
Figure 28:
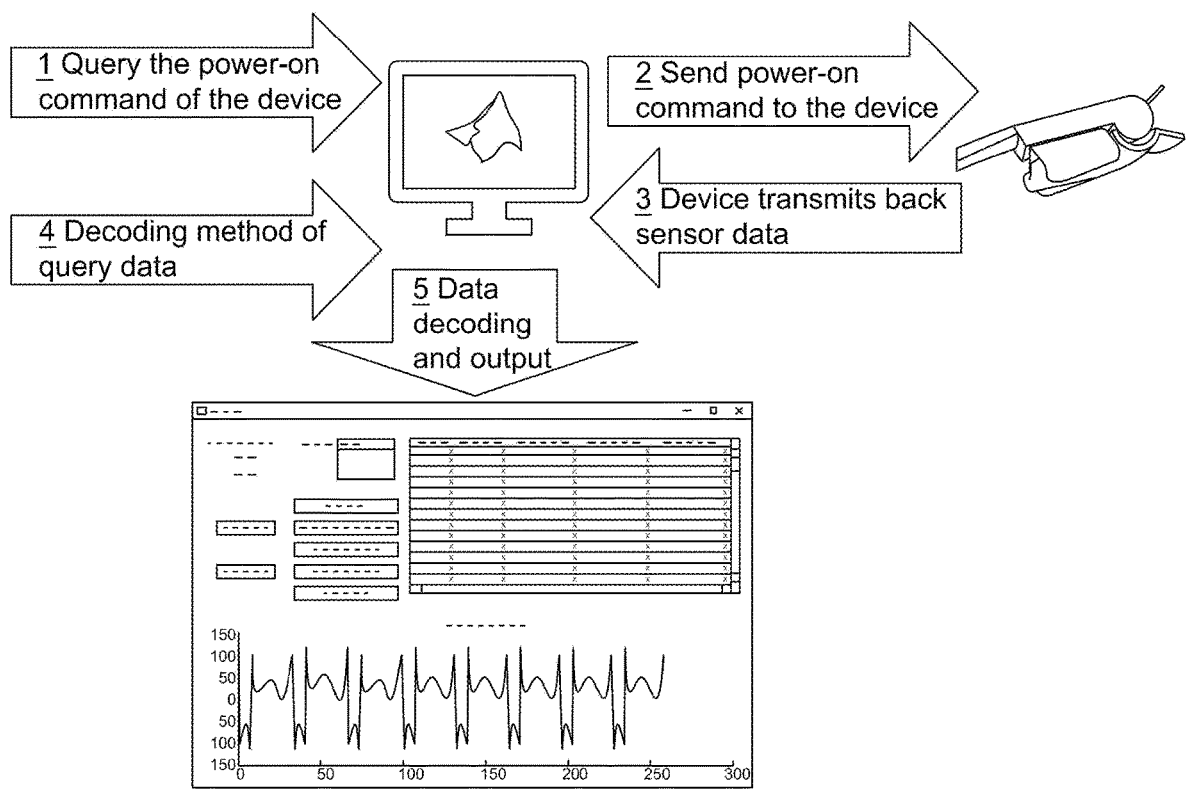
FIG. 28 is a device-software outline for a typical and exemplary operation of the preferred embodiment of the present invention.

In the method of predicting the type of blood vessel from the acceleration pulse wave, the vascular health condition is calculated by the ratio of peak to the second derivative of blood volume pulse wave. Accurate diagnosis of the condition of blood vessels can be discerned by the ratio of peak to the second derivative. Difficult cases may arise, and the results may vary with each measurement, resulting in poor reliability as a diagnostic device. Thus, there is a need for a method for more accurately and reliably diagnosing vascular conditions using acceleration pulse waves. In addition, there is a need to detect various health indices such as vascular age, vascular health index, and arteriosclerosis by detecting the state of blood vessels. Accordingly, as best shown in conjunction with FIG. 27 and FIG. 28, the present invention provides a method for detecting an accurate vascular health condition by detecting a waveform of a PPG signal and converting the waveform into a derivative function of various orders to quantify the degree of blood circulation.

Figure 29:
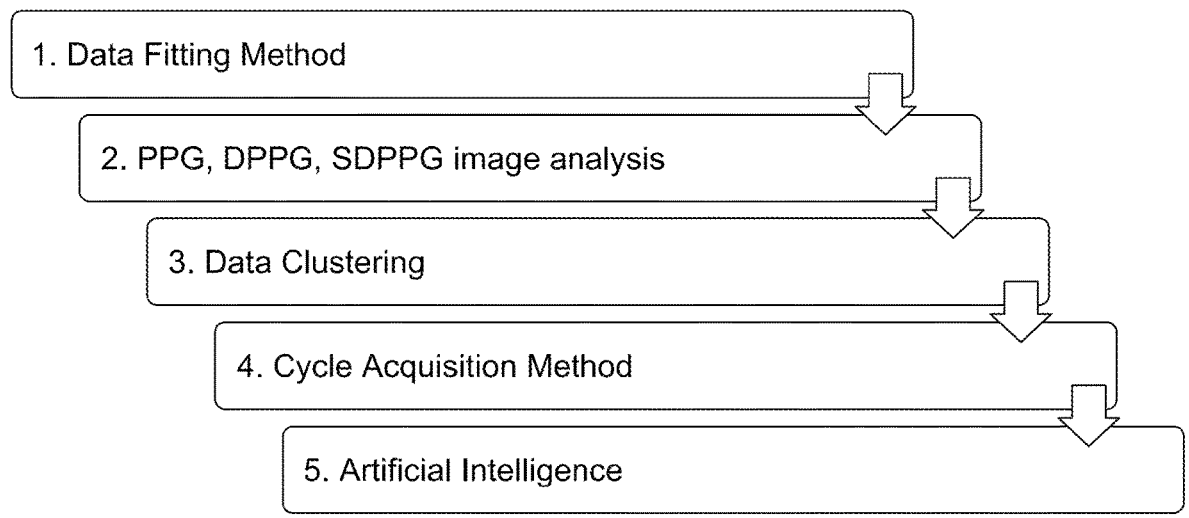
FIG. 29 is a flow diagram depicting a Verified Algorithm paired with AI Quintuple Layers of Analysis according to the preferred embodiment of the present invention.

In operation the improved pulse wave velocity detection device of the present invention may be uses as part of a wide variety of non-invasive screening testing in a number of areas. Various algorithms may be used to optimize the accuracy of readings from the finger-type PPG (optical) sensor device. As shown in conjunction with FIG. 29, analyses of the SI and Ax index within the present invention consists essentially of five layers of processing: data fitting method; image analysis; data clustering; cycle acquisition method; and artificial intelligence.

The data fitting method preferably obtains a plurality of time spaced pulse points to form a line. In a more preferred embodiment, initial data collection involved the capture of the individual patient's pulse information connected to form the curve or wave form. The device may collect multiple separate pulse points over time and connects them into a line to form the PPG Image. In a preferred embodiment, the device may collect sixty-four (64) separate pulse points every 1.28 seconds to generate the line forming the PPG Image. Data filtering was done to remove extreme outlier points, and the remaining good fit data used for further calculation. This method however, posed challenges as the making any subtle movement while the patient is being measured captured by the device (i.e., with the device captured one pulse point every 0.02 seconds, subtle movements may generate "noise" errors). This may cause the data collected by the device to be susceptible to interference, and irrelevant noise. Various statistical filtering tools such as averaging was used in the calculation process to reduce interference, but that was not enough for high accuracy readings.

Figure 30:
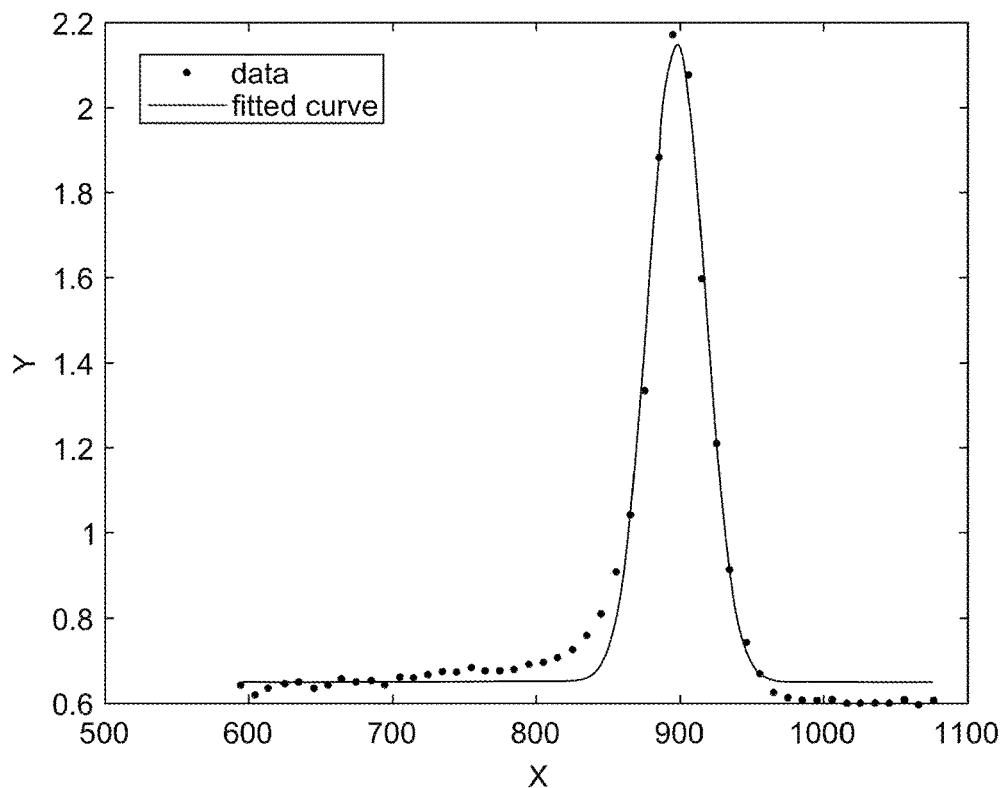
FIG. 30 is a graphical representation of a Data Fitting Process according to the preferred embodiment of the present invention.
Figure 31:
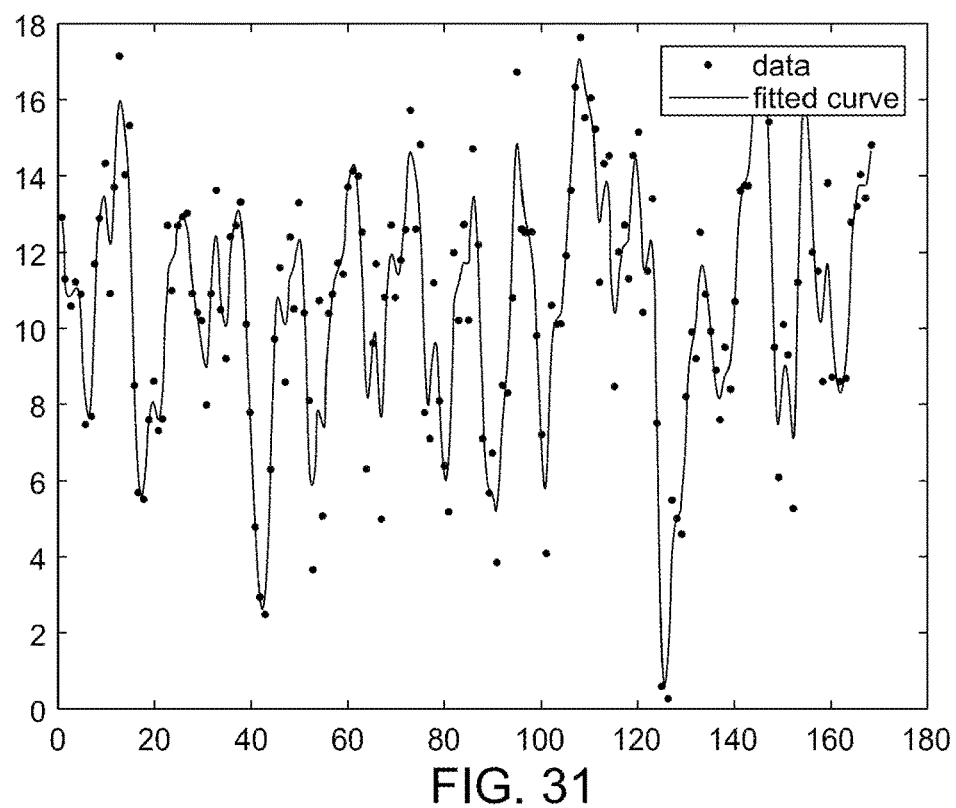
FIG. 31 is a graphical representation of a Fitted Curve for use therewith.

An improved solution may fit the data collected through a modelled fitting process as best shown in conjunction with FIG. 30 and FIG. 31. The data fitting process uses each pulse point in an image and find a curve that best represents all the points instead of the original pulse points. The fitted curve is able to analyze the image shape as a whole, which is more effective than the original way of directly connecting and then filtering.

Another challenge noticed after the data fitting process was some peak values were cut-off and represented as very low digits as can be seen in FIG. 30. This issue was resolved by recalibrating the peaks of the device and adding 256 to the values of the very-low recorded data. This fixed all cut-off points to their supposed locations on the curve. It was still noticed that the accuracies of the readings were not optimum, hence the need for another algorithm to collect the data in periodic cycles.

The original acquisition method was based on a linear acquisition method, which is susceptible to fluctuations in patient posture changes. Any slight change in the patient's posture caused a dramatic change in the data.

Figure 32:
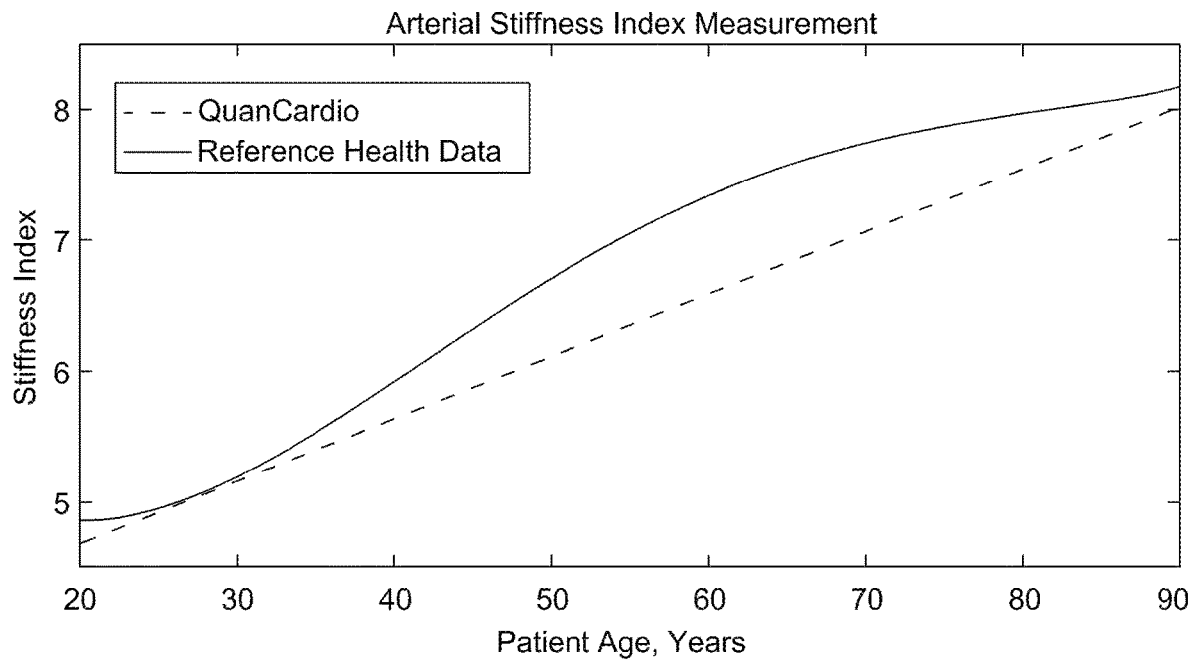
FIG. 32 is a graphical representation of arterial stiffness trends for use therewith.
Figure 33:
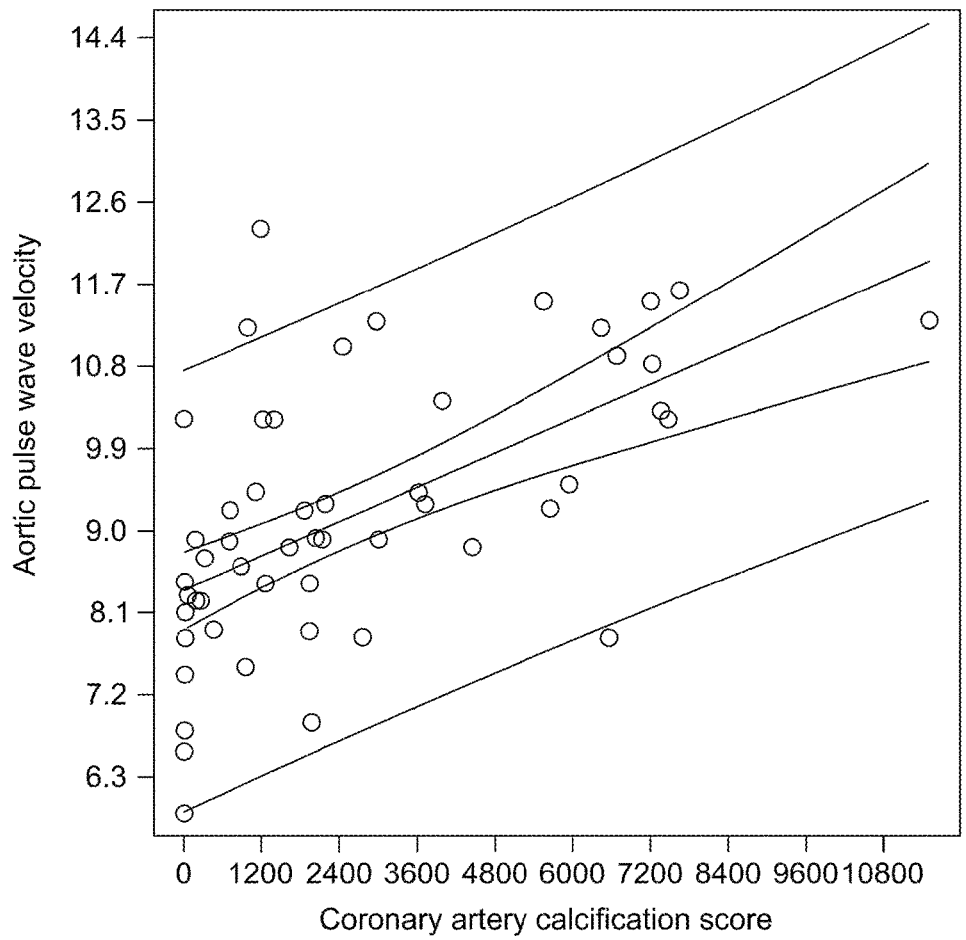
FIG. 33 is a graphical representation of Arterial Deposits (CAC) score trends with Aortic PWV for use therewith.

The use of cycle acquisition method excluded abnormal cycle data and ensure correct data acquisition. The periodic cycle acquisition method is to decompose the PPG images into small cycles, analyze the images of each small cycle individually, and finally average all the cycle images for calculation. In the periodic cycle method, firstly, the PPG image is decomposed into smaller images according to the cycle. As shown in conjunction with FIG. 32 and FIG. 33, the PWV, PTT, ADS (CAC), Aging Index (AGI) and other parameters are individually for each small image. The values calculated for each cycle are then averaged and distributed to obtain the average.

The initial AGI method called the slope method which was further advanced to the wave-point method, would be further explored with the AI techniques, however, at the beginning stages, this method was not helpful. By comparing newly obtain images with historical records of other patients, different patterns and their association with other general health data can be correlated to arrive at a diagnosis. Using differential diagnostics, the AI comparison may become more accurate and robust over time. With the slope method, each wave was to be considered based on the shape of the wave, with the slope of the first minimum and the second minimum of each cycle determined the health of the patient's blood vessels. The larger the slope, the healthier the blood vessel; the smaller the slope, the more senile the vessel.

Figure 34:
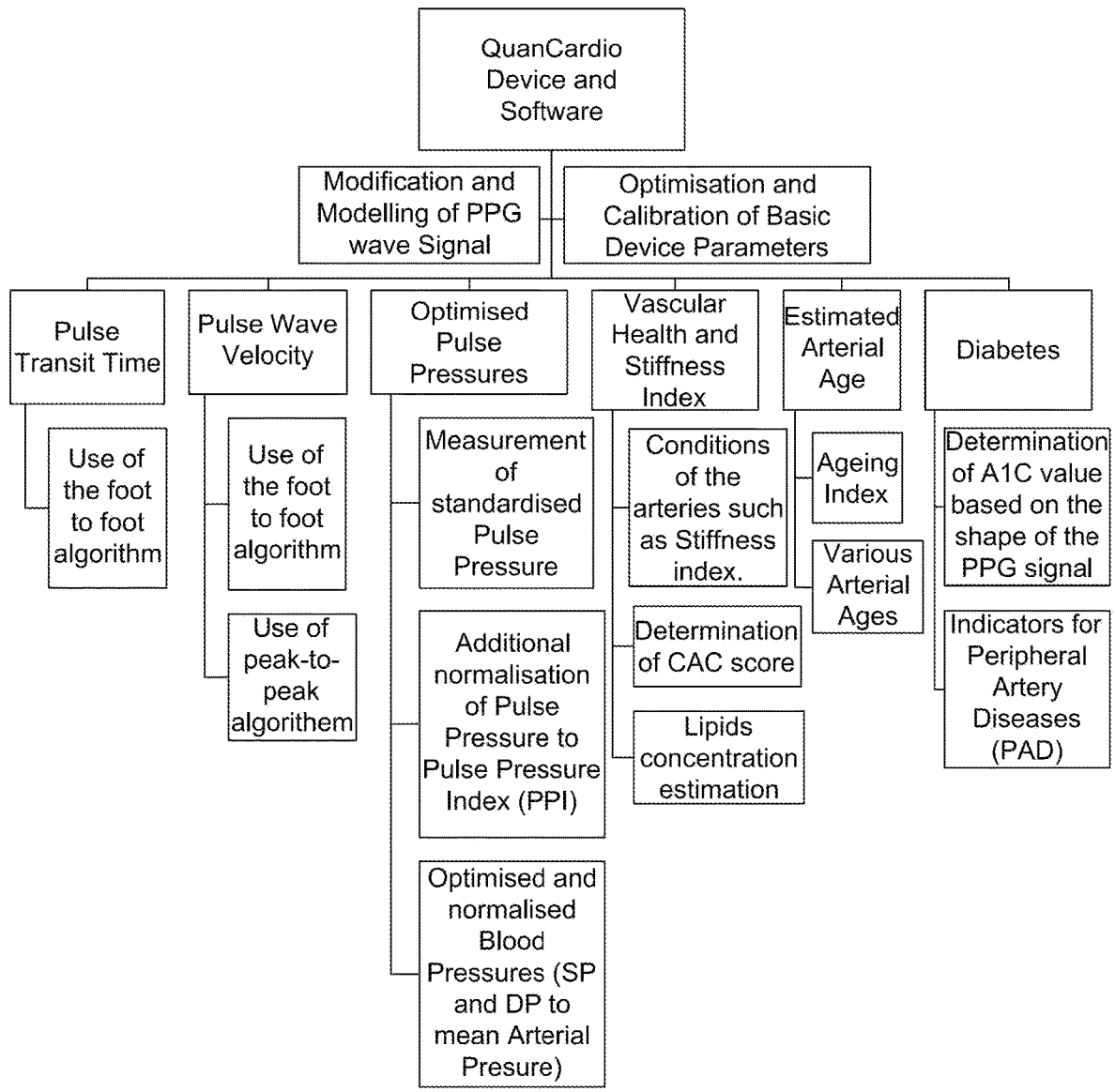
FIG. 34 is a block diagram of the QuanCardio Algorithm for use therewith.
Figure 35:
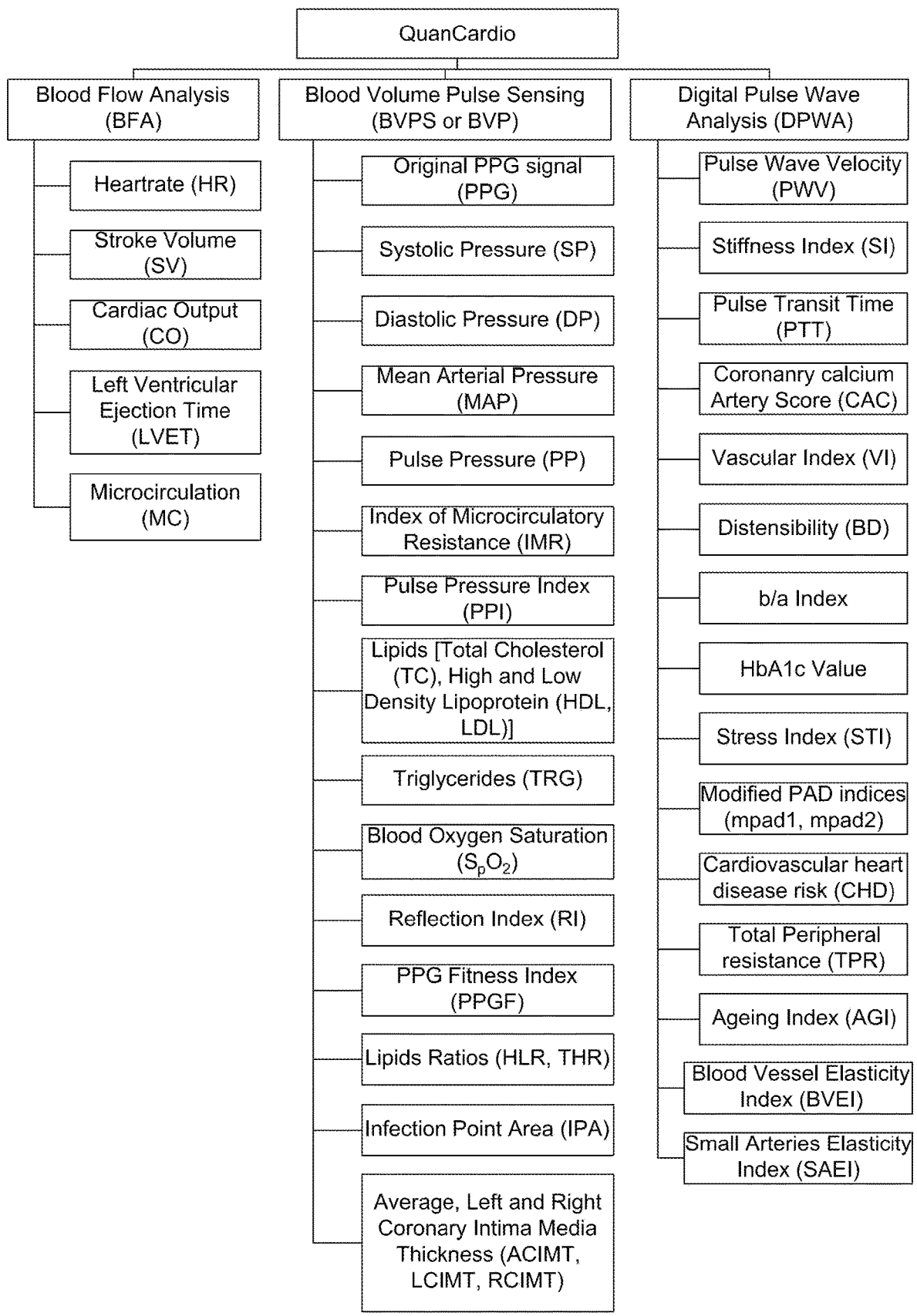
FIG. 35 is a block diagram of the QuanCardio Parameters Analysis for use therewith.
Figure 36:
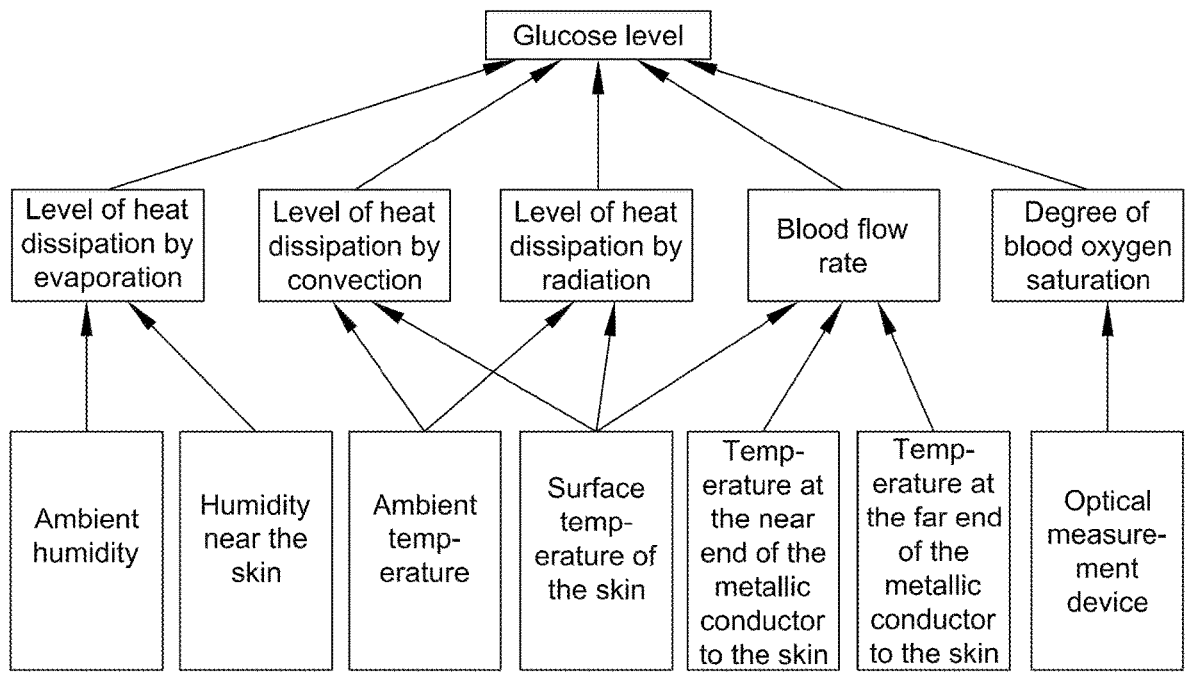
FIG. 36 is a block diagram of an alternate function of the present invention outlining the method for measuring metabolic heat to determine a glucose level.
Figure 37:
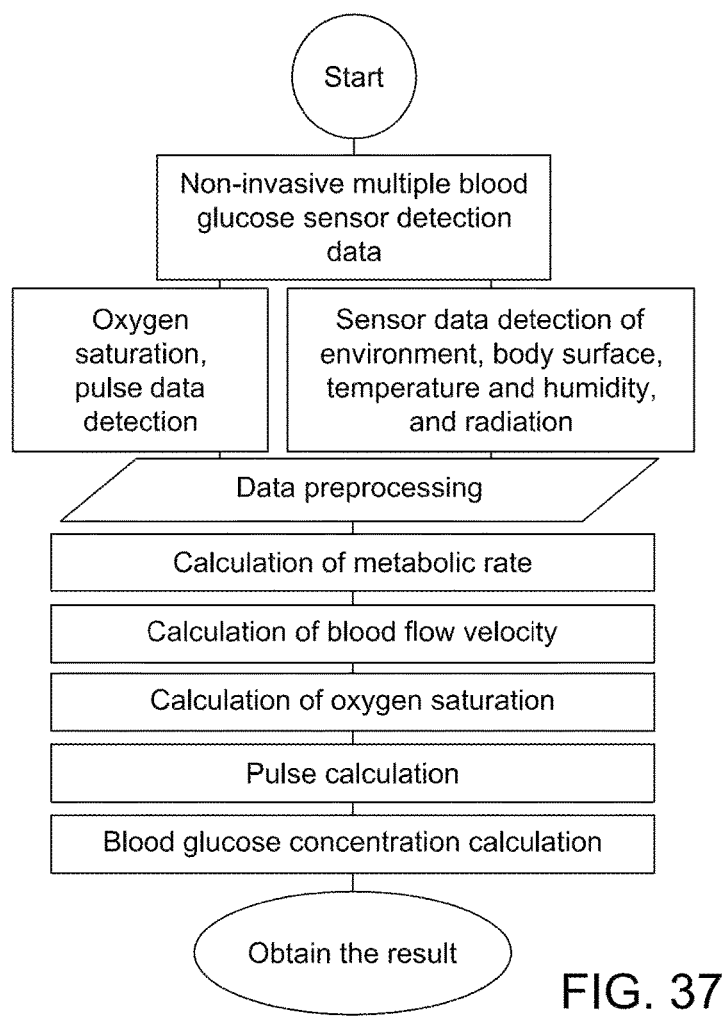
FIG. 37 is a block diagram for a method for measuring metabolic heat.

Data Clustering is performed using a decision tree to match the PPG images read by the device to one of the seven classes of arterial stiffness. Period cycling method excludes abnormal cycle data and ensure correct data acquisition. Artificial Intelligence Image comparison and data analytics helps the software get smarter with every patient. Comparing images with images of other patients and general health data to identify patterns. Using differential diagnostics to arrive at a correct diagnosis. These algorithms can be summarized as shown in FIG. 34. Further analysis on parameters can also be summarized as shown in FIG. 35.

It should be understood that the legal scope of the description is defined by the words of the claims set forth at the end of this patent and that the detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims. By way of example, and not meant as a limitation, according to another aspect of the present invention, the development of such a non-invasive sensor may be further adapted for measuring glucose levels directly through the measurement of oxygen saturation deduced through metabolic heat. Such an adaptation would result in the first non-invasive glucose meter for continuously monitoring and analyzing blood glucose levels. Adapting the described non-invasive hardware may provide a non-invasive glucose measurement technology using metabolic heat conformation and optical methodology. Such a non-invasive portable glucose meter may integrate various sensors for signal collection, a processing circuit for signal conversion and amplification, and a microprocessor to calculate the values of the parameters (such as blood glucose concentration, oxygen saturation, hemoglobin concentration, blood flow volume, pulse, ambient temperature and humidity, and shell temperature and humidity), and to display the measurement results.

The principle of operation for such a device adaptation provides two parameters, oxygen saturation, and hemoglobin (Hb) concentration, which are measured using photoelectric methods. Infrared lights of specific wavelengths irradiate the skin surface of fingers at a fixed time series. Subsequently, the luminous intensity through the finger is measured and used to calculate the required parameter information. Heat dissipation cannot represent local metabolic heat; thus, core temperature, resistance of clothes, and blood flow volume are used to correct the local metabolic heat. The metabolic heat integration method's blood glucose value is calculated using local metabolic rate, blood flow volume, Hb concentration, oxygen saturation, and normalized blood glucose. Photoelectric signals and Hb concentration are used to obtain infrared-based blood glucose values.

The metabolic oxidation of glucose in the human body, also known as cellular respiration, provides the energy necessary for cellular activities. Non-invasive glucose concentration measurements in the blood consider the body heat generated by glucose oxidation and local oxygen supply. This concept was developed by observing that the human body's circadian rhythm conforms to the subtle balance among metabolic heat, local oxygen supply, and glucose concentration. As best shown in conjunction with FIG. 27 and FIG. 28, the system may be adapted to provide three temperature sensors, two humidity sensors, an infrared sensor, and an optical measurement device. The glucose level can be deduced from the quantity of heat dissipation, blood flow rate of local tissue, and degree of blood oxygen saturation.

The two parameters, oxygen saturation and Hb concentration may be measured using photoelectric methods. Infrared lights of specific wavelengths irradiate the skin surface of fingers at a fixed time series. Subsequently, the luminous intensity through the finger is measured and used to calculate the required parameter information. Heat dissipation cannot represent local metabolic heat; thus, core temperature, resistance of clothes, and blood flow volume are used to correct the local metabolic heat. The metabolic heat integration method's blood glucose value is calculated using local metabolic rate, blood flow volume, Hb concentration, oxygen saturation, and correct blood glucose. Photoelectric signals and Hb concentration are used to obtain infrared-based blood glucose values.

The foregoing descriptions of specific embodiments of the present invention are presented for illustration and description. The disclosure's Title, Background, Summary, Brief Description of the Drawings, and Abstract are hereby incorporated into the disclosure and provided as illustrative examples, not as restrictive descriptions. It is submitted with the understanding that they will not be used to limit the scope or meaning of the claims. In addition, in the Detailed Description, it can be seen that the description provides illustrative examples, and the various features are grouped in various embodiments to streamline the disclosure. This method of disclosure is not to be interpreted as reflecting an intention that the claimed subject matter requires more features than are expressly recited in each claim. Instead, as the following claims reflect, the inventive subject matter is less than all features of a single disclosed configuration or operation. The following claims are incorporated into the Detailed Description, with each claim standing as a separately claimed subject matter.

What is claimed is:

1. A pulse wave velocity detection system for analyzing arterial datum, comprising:
    a pulse wave velocity detection device comprising a finger-type Photoplethysmogram (PPG) optical sensor device comprising a photodiode and a resistor for capturing arterial data using a location of data acquisition;
    an analog side in communication with a digital side to generate pulse waves at a specific baud rate, wherein the pulse wave velocity detection device analyzes one of the generated pulse waves in the time domain to extract features related to arterial stiffness;
    a central control chip in operational connection with a pulse acquisition unit comprising a photosensitive assembly, the photosensitive assembly comprising the photodiode and the resistor, the resistor connected with the photodiode in parallel, with two ends of the photodiode connected with the central control chip; and
    the pulse wave velocity detection system configured to utilizing patient height and weight as algorithm modifiers for accurate arterial data analysis.

2. The pulse wave velocity detection system of claim 1, wherein the pulse wave velocity finger-type Photoplethysmogram (PPG) optical sensor detection device captures pulse wave velocity to measure status of heart and blood vessels, arterial wall stiffness, biological age of arteries and detects different stages of cardiovascular disease and diabetes management by analyzing volumetric blood flow pulsation signals.

3. The pulse wave velocity detection system of claim 1, wherein the pulse wave velocity finger-type Photoplethysmogram (PPG) optical sensor detection device further comprises an algorithm software for non-invasively and rapidly measuring HbA1C, arterial stiffness, arterial age, or arterial deposits.

4. The pulse wave velocity detection system of claim 1, wherein the PPG optical sensor detection device is used in both reflection and transmission modes, wherein in the reflection mode a light source and photodetector are positioned in parallel, enabling measurement of backscattered light from a skin surface.

5. The pulse wave velocity detection system of claim 1, wherein the pulse wave velocity detection device captures pulse wave velocity to measure status of heart and blood vessels, arterial wall stiffness, biological age of arteries and detects different stages of cardiovascular disease and diabetes management by analyzing volumetric blood flow pulsation signals.

6. The pulse wave velocity detection system of claim 1, wherein the pulse wave velocity detection device further comprises an algorithm software for non-invasively and rapidly measuring HbA1C, arterial stiffness, arterial age, or arterial deposits.

7. The pulse wave velocity detection system of claim 1, wherein the PPG optical sensor device is used in both reflection and transmission modes, wherein in the reflection mode a light source and photodetector are positioned in parallel, enabling measurement of backscattered light from the skin surface.

8. A pulse wave velocity detection system for analyzing arterial data, comprising:
    a pulse wave velocity detection device comprising a finger-type Photoplethysmogram (PPG) optical sensor device for capturing arterial data using a location of data acquisition;
    an analog side in communication with a digital side to generate pulse waves at a specific baud rate, wherein the pulse wave velocity detection device analyzes one of the generated pulse waves in the time domain to extract features related to arterial stiffness;
    a central control chip in operational connection with a pulse acquisition unit comprising a photosensitive assembly, the photosensitive assembly comprising a photodiode and a resistor, the resistor connected with the photodiode in parallel, with two ends of the photodiode connected with the central control chip; and
    the pulse wave velocity detection device utilizing patient height and weight as algorithm modifiers for accurate arterial data analysis.

* * * * *